(12) United States Patent
Glick et al.

(10) Patent No.: US 12,374,441 B2
(45) Date of Patent: Jul. 29, 2025

(54) AI-ASSISTED TREATMENT OPTIMIZATION LEVERAGING TREATMENT FIDELITY DATA

(71) Applicant: Behavior Science Technology, Inc., New London, NH (US)

(72) Inventors: Troy Glick, New London, NH (US); Patricia Glick, New London, NH (US); Abigail Burela, Poughkeepsie, NY (US); Kerry Conde, Lake Ronkonkoma, NY (US); Duane Jung, Cornelius, NC (US)

( * ) Notice: Subject to any disclaimer, the term of this patent is extended or adjusted under 35 U.S.C. 154(b) by 0 days.

(21) Appl. No.: 18/653,395

(22) Filed: May 2, 2024

(65) Prior Publication Data

US 2024/0387020 A1 Nov. 21, 2024

Related U.S. Application Data

(60) Provisional application No. 63/550,531, filed on Feb. 6, 2024, provisional application No. 63/467,999, filed on May 21, 2023.

(51) Int. Cl.
*G16H 20/70* (2018.01)
*A61B 5/16* (2006.01)
*G16H 10/60* (2018.01)
*G16H 40/20* (2018.01)

(52) U.S. Cl.
CPC ............. *G16H 20/70* (2018.01); *A61B 5/165* (2013.01); *G16H 10/60* (2018.01); *G16H 40/20* (2018.01)

(58) Field of Classification Search
None
See application file for complete search history.

(56) References Cited

U.S. PATENT DOCUMENTS

| | | | | |
|---|---|---|---|---|
| 11,178,253 | B2 | 11/2021 | Ward | |
| 11,195,619 | B2 * | 12/2021 | Baughman | G06N 20/00 |
| 2007/0088577 | A1 * | 4/2007 | Carter | G16H 10/60 |
| | | | | 705/3 |
| 2011/0184781 | A1 * | 7/2011 | Hussam | G16H 40/20 |
| | | | | 705/7.32 |
| 2012/0239430 | A1 * | 9/2012 | Corfield | G06Q 10/06 |
| | | | | 705/3 |
| 2016/0019813 | A1 * | 1/2016 | Mullen | G16H 15/00 |
| | | | | 434/236 |
| 2016/0054023 | A1 * | 2/2016 | Baker | F24F 11/30 |
| | | | | 315/307 |
| 2016/0091877 | A1 * | 3/2016 | Fullam | G06T 19/006 |
| | | | | 700/275 |

(Continued)

OTHER PUBLICATIONS

Wohofsky et. al., "Requirements of a Supportive Environment for People on the Autism Spectrum: A Human-Centered Design Story", Applied Sciences 2023, 13 1899; published Feb. 1, 2023 (Year: 2023).*

*Primary Examiner* — Anne-Marie K Alderson

(57) ABSTRACT

Techniques described herein leverage recent advances in artificial intelligence to enable generating new analyses and insights based on comprehensive data sets that include treatment fidelity data related to patients. These new analyses and insights may be used to then provide better clinician feedback and/or better customization of treatment plans for patients, thereby improving outcomes for patients while also improving the ability of clinicians to provide effective care.

19 Claims, 5 Drawing Sheets

(56) References Cited

U.S. PATENT DOCUMENTS

| | | |
|---|---|---|
| 2021/0217516 A1* | 7/2021 | Nash .................. G16H 50/30 |
| 2021/0257081 A1 | 8/2021 | Etra et al. |
| 2023/0021336 A1* | 1/2023 | Troxler ................ G06N 5/022 |
| 2023/0075466 A1* | 3/2023 | Robaina ............... A61B 5/1171 |
| 2024/0087705 A1* | 3/2024 | Etra ................... G16H 20/70 |

* cited by examiner

AI-ASSISTED TREATMENT OPTIMIZATION LEVERAGING TREATMENT FIDELITY DATA

PRIORITY CLAIM

This application claims priority to provisional applications 63/467,999 (filed May 21, 2023) and 63/550,531 (filed Feb. 6, 2024), both of which are hereby incorporated by reference in their entirety.

FIELD

The present disclosure relates to treatment of conditions including developmental disorders, of which an example use case is the treatment of autism spectrum disorder (ASD), using machine learning and artificial intelligence.

BACKGROUND

Previous attempts to improve the treatment of ASD and other disorders using machine learning and related technologies have failed to demonstrate effectiveness. These attempts have frequently lacked nuance and explanatory power, and therefore are insufficient for robustly improving treatment outcomes. More effective treatment improvements require collecting the right data sets and using them in more effective ways.

SUMMARY

A system/device as described herein may execute (using one or more processors) a computer-implemented method, which may include receiving patient data for a patient being treated for autism spectrum disorder (ASD) or another condition or conditions. The patient data may include medical data for the patient, environmental data indicating environmental conditions of the patient, behavioral health data for the patient, outcome data indicating one or more outcomes for the patient. The system or device may also receive, from one or more sensors, sensor data during a behavioral treatment session involving a care provider for the patient.

The system/device may receive or generate treatment fidelity data for the patient. If the system or device generates the treatment fidelity data, it may generate the treatment fidelity data based on the sensor data from the one or more sensors. The treatment fidelity data may be generated using a first machine learning model. The generated treatment fidelity data may include a plurality of indicators of whether the care provider is following a treatment plan for the behavioral treatment session.

The systems/devices may generate, based on the patient data and/or the treatment fidelity data, a plurality of treatment fidelity scores including a clinical score that is indicative of whether the care provider is accurately following clinical procedures, an environmental score that is indicative of environmental conditions that may interfere with the behavioral treatment session, and a professionalism score that is indicative of professionalism of the care provider. In some cases, the treatment fidelity scores may be generated using a machine learning model.

The systems/devices may determine, based on any of the treatment fidelity scores, that a treatment plan is not optimized. The systems or devices may then generate, using a predictive analytics model, based on the patient data, an optimized treatment plan. The optimized treatment plan may include a modified treatment schedule or some other modification. The systems or devices may transmit an instruction to adopt the optimized treatment schedule.

In some cases, the optimized treatment schedule may include a future treatment session with a different care provider. In these cases, predictive analytics may comprise matching the patient with the different care provider based on the patient data and a respective treatment fidelity score associated with the different care provider.

In some cases, the one or more sensors may include a video sensor, and the first machine learning model may be a multimodal model that accepts image data. Additionally or alternatively, the one or more sensors may include an audio sensor, and the first machine learning model may be a language model.

In some cases, determining that the treatment plan is not optimized may comprise detecting a reduction and/or change in any of the treatment fidelity scores.

The computer-implemented method may further include determining, based on an environmental score, that the environment is not optimized for treatment. The method may then include detecting, based on the environmental data, an individualized pattern indicating a correlation between an environmental condition and a personalized patient factor. The method may further include generating, based on the individualized pattern, an instruction to adjust the environment by controlling a machine in the vicinity of the behavioral treatment session. The method may then include transmitting the instruction to the machine.

Another computer-implemented method may include receiving patient data for a patient being treated for a condition, where the patient data comprises environmental data collected by sensors during treatment. The method may further include receiving treatment fidelity data including a plurality of indicators of whether the care provider is following a treatment plan for the behavioral treatment session. The method may further include generating, based on the patient data and the treatment fidelity data, using a machine learning model, a plurality of treatment fidelity scores including an environmental score that is indicative of environmental conditions that may interfere with the behavioral treatment session. The method may further include determining, based on the environmental score, that the environment is not optimized for treatment. The method may further include detecting, based on the environmental data, an individualized pattern indicating a correlation between an environmental condition and a personalized patient factor. The method may further include generating, based on the individualized pattern, an instruction to adjust the environment by controlling a machine in the vicinity of the behavioral treatment session. The method may further include transmitting the instruction to the machine. In some cases, the machine is a thermostat that controls heating or cooling. Additionally or alternatively, the machine may be an automation system that controls lighting. In some cases, the personalized patient factor may be an indicator of an increase in stress levels for the patient. Additionally or alternatively, the personalized patient factor may be an indicator of a decrease in treatment effectiveness for the patient.

Another computer-implemented method may include receiving patient data for a patient being treated for a condition. The method may further include receiving, from one or more sensors, real-time sensor data during a behavioral treatment session involving a care provider for the patient being treated for the condition. The method may further include generating treatment fidelity data based on the real-time sensor data from the one or more sensors, wherein the treatment fidelity data is generated using a first machine learning model, wherein the generated treatment fidelity data includes a plurality of indicators of whether the care provider is following a treatment plan for the behavioral treatment session. The method may further include detecting, based on the treatment fidelity data, that the care provider did not correctly follow the treatment plan for the behavior treatment session. The method may further include generating, using a machine learning model, a prompt for correcting the care provider. The method may further include transmitting, to the care provider, the prompt for correcting the care provider. The method may further include receiving additional real-time sensor data after transmitting the prompt. The method may further include verifying, based on the additional real-time sensor data, that the care provider correctly followed the treatment plan based on the prompt.

These and other methods may be combined in various ways; for example, the systems/devices as described herein may implement each of the above methods. Although the above-described computer-implemented methods are exemplary of some of the features of the systems/devices described herein, other computer-implemented methods are described below. A more complete understanding of the disclosure will be appreciated from the description and accompanying drawings and the claims, which follow.

BRIEF DESCRIPTION OF THE DRAWINGS

The accompanying drawings, which are included to provide a better understanding of the disclosure, illustrate embodiment(s) of the disclosure and together with the description serve to explain the principle of the disclosure. In the drawings.

DETAILED DESCRIPTION

Figure 1:
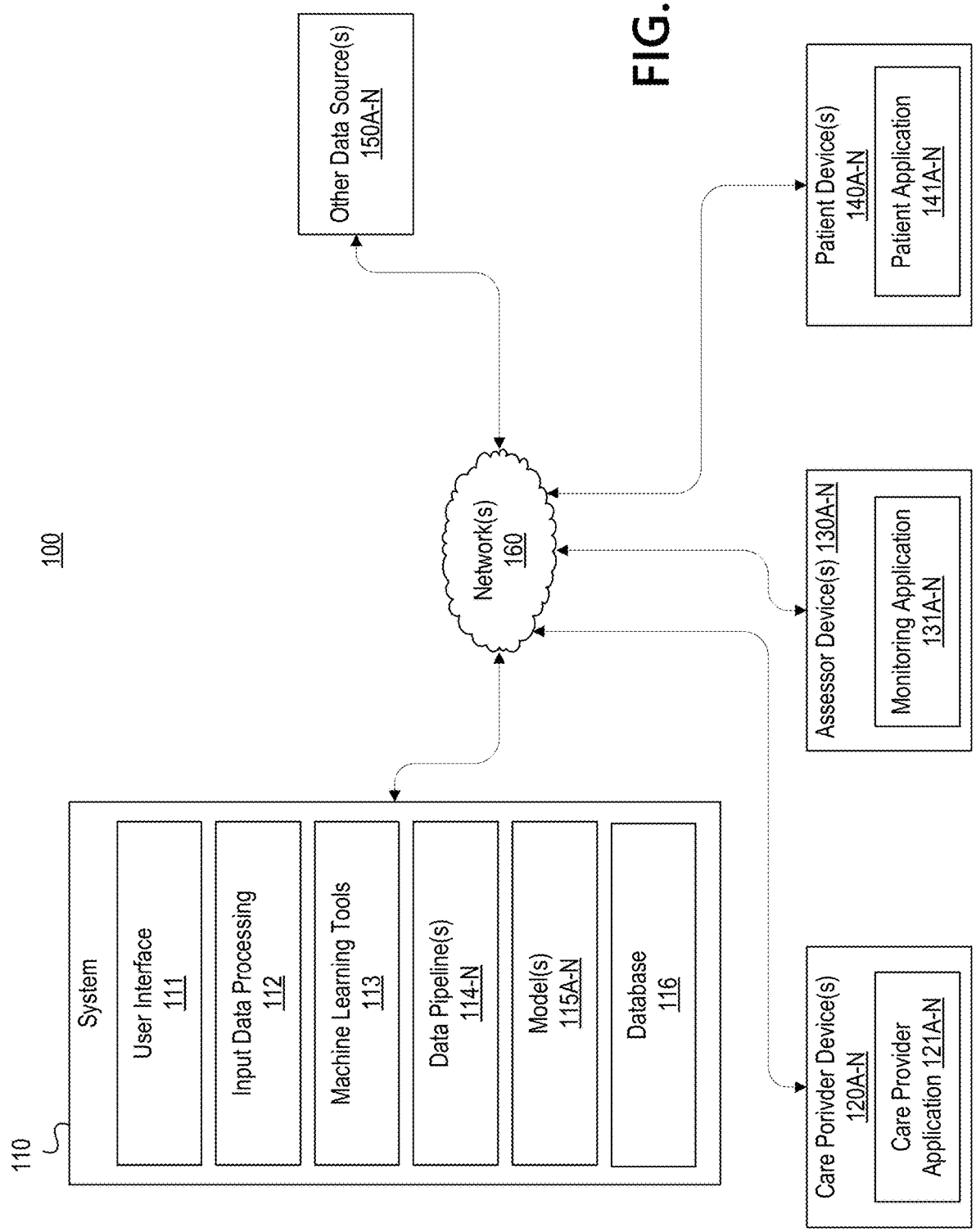
FIG. 1 illustrates an example environment including various systems described within the present disclosure.

Techniques described herein leverage recent advances in artificial intelligence techniques to enable generating new analyses and insights comprehensive data sets that include treatment fidelity data related to patients. These new analyses and insights may be used to then provide better clinician feedback and/or better customization of treatment plans for patients, thereby improving outcomes for patients while also improving the ability of clinicians to provide effective care.

Several of the techniques describe herein leverage treatment fidelity data that measures how closely a particular treatment plan was followed, what types of errors may have been made by a clinician, what types of deviations from the plan occurred, who caused the deviations, and/or other such metrics. This data on its own is valuable for measuring the accuracy of treatment, but the techniques described herein provide improvements to treatment outcomes by combining this data with other data including patient outcome data, environmental data, and/or other types of data that may be collected about patients. By correlating diverse data and generating comprehensive data sets, then analyzing the comprehensive data sets using artificial intelligence techniques, the system may be able discover unique patterns (e.g., patient-specific responses to treatment plans), generate better care provider feedback, generate better predictive analytics, and better customize treatment plans, among other benefits. By contrast, conventional approaches may involve simply gathering patient and outcome data and attempting to make predictions therefrom. These approaches lack the insights provided by treatment fidelity data in combination with other diverse data sources and thereby may fail to detect unique patterns, may provide poorer feedback, may provide worse predictions, and may not accurately tailor treatment plans to individuals.

The approaches described herein may have particular applicability in contexts in which a patient may have difficulty communicating with a care provider, such as autism spectrum disorder (ASD) in children. In these and similar contexts, the patient may be unable to perform certain skills and/or unwilling to perform other skills, but it may be difficult for care providers to determine why certain approaches fail while others succeed. Another applicable context is treatment of a patient in a hospital intensive care unit (ICU) where the patient cannot communicate due to some condition or injury, or other contexts in which a patient may have difficulty in communicating. Additionally, these techniques may be useful in tiered systems, where the care provider primarily follows a directive and does not necessarily respond to the patient, except in specific situations such as delivering a reinforcer. More broadly, patients may be unaware of why they respond well or poorly to treatments in other medical contexts. The techniques described herein involve collecting sufficient data to enable the detection of why a patient responds well or poorly to a given treatment and then performing unique analyses that involve treatment fidelity data to optimize treatment and ultimately improve outcomes.

The use of treatment fidelity data together with other data as described herein does not only enable more accurate analyses and predictions, but also enables entirely new AI models that may perform advanced functions to assist care providers in better caring for particular patients. Several of these models and functions are described in more detail below.

Computing Environment

FIG. 1 shows an environment 100 including components that carry out methods and operations as described in more detail below. The environment 100 may include a plurality of devices that comprise a system 110, various devices 120A-N, 130A-N, and 140A-N, and one or more other data sources 150A-N, where the plurality of devices are connected via one or more network(s) 160. The network connections shown are illustrative and any means of establishing communications links between the various devices may be used. The existence of any of various network protocols such as TCP/IP, Ethernet, SFTP, HTTPS and the like, and of various wireless communication technologies such as GSM, CDMA, Wi-Fi, LTE, 5G, etc., is presumed, and the various computing devices described herein may be configured to communicate using any of these network protocols or technologies.

The system 110 may itself include a plurality of devices or components, including one or more user interfaces 111, input data processing 112, machine learning tools 113, one or more data pipelines 114, a plurality of models 115, and a database 116. In general, the system 110 may provide functionality to the various devices 120, 130, 140 that allows users of the devices to provide various data and/or receive information (e.g., via a user interface 111) as explained in more detail below.

The care provider devices 120 may be user devices used by various care providers (e.g., board certified behavior analysts (BCBAs) and/or behavior technicians) to interact with the system via an application 121 on each device. For example, a care provider may use a device 120A to log data about patients, to interact with a user interface 111 provided by the system 110, and the like.

The assessor devices 130A-N may be used by assessors (e.g., BCBAs that monitor behavior technicians, or supervisors that monitor BCBAs) to monitor the provision of treatment by care providers (which may be BCBAs, behavior technicians, etc., depending on circumstance), log treatment fidelity data, and/or the like. Additionally or alternatively, the assessor devices may, in some cases, be configured to capture data via sensors that may be used to detect treatment fidelity issues and/or correlated with treatment fidelity data. In these situations, the devices 130 themselves may carry out the role of assessors. In other words, the term "assessors" as used herein may encompass human users that are observing and/or assessing treatment by care providers and/or machines that fill the assessor role in an automated or semi-automated way. The use of devices to automatically capture treatment fidelity data and other data via sensors is described in more detail below.

The patient devices 140A-N may include devices used by patients, which may be devices for collecting objective environmental, behavioral or health related measurements, inputting patient information, and/or logging patient information. In some cases, the environment 100 may also include devices used by family members of the patient (not shown), who may also provide patient information, such as medical records, behaviors and other such information as listed in more detail below.

The various devices 120, 130, 140 may include mobile devices (e.g., smartphones, laptops, tablets), wearable devices (e.g., smartwatches, VR/AR/XR headsets, biometric sensors), other computing devices (e.g., desktop computers, servers), and/or any other devices that may run and interact with corresponding applications 121, 131, 141. In embodiments, the applications may communicate with the system 110, which may provide a client/server user interface that allows respective users of the devices to interact with the system 110. Additionally or alternatively, the applications may perform some of the features and functionalities ascribed to the system 110, such that the system may be partially or completely decentralized by performing any of the operations described herein locally on the devices 120, 130, and/or 140. In embodiments, the applications 121, 131, 141 may be one of various web browsers, which may be used interchangeably. Additionally or alternatively, the applications may include various applications that may be native to various operating systems, such as a WINDOWS client application, a MacOS client application, an iOS mobile application, an Android mobile application, etc. The applications 121, 131, 141 may take advantage of various inputs, such as mouse and/or keyboard, touchscreen inputs, voice inputs (e.g., using speech to text software), and/or any other interaction method for inputting data, instructions, selections, and the like.

In embodiments, the system 110 may include one or more computing devices that may implement one or more respective servers, databases, etc. In embodiments, the system 110 may be implemented using a cloud services provider, which may manage the distribution of tasks and/or workloads across the various computing devices. The computing device(s) making up the system 110 may execute the methods and operations described herein using serial, parallel, hierarchical, and/or other computing techniques. For example, a first computing device may distribute sub-tasks of a task to various computing devices of the system (e.g., when the sub-tasks are parallelizable), may balance workloads between the computing devices, and the like. Thus, although the system may be described as a single entity, the system may use a plurality of computing devices working in coordination to complete the tasks described herein.

The environment 100 may further include other data sources 150A-N, which may include third party data sources, providers of medical records databases, providers of remotely executed models or other AI services, and/or the like. These sources 150 may provide any of the data, features, or functionalities described herein outside of the system 110.

The database 116 within the system 110 may be implemented via various cloud services, via database servers, and/or the like. The database 116 may include, but is not limited to, one or more relational databases, hierarchical databases, distributed databases, in-memory databases, flat file databases, XML databases, SQL databases, NoSQL databases, graph databases, and/or a combination thereof.

The model(s) 115 may include various types of models that may be run locally by the system 110 and/or via remote servers. Some of the models 115 may be fine-tuned pre-trained models (e.g., large language models or other generative AI models) provided by third parties. In some cases, models 115 may include multi-modal models that may be capable of receiving inputs and/or generating outputs that include various types of data, such as text data, audio data, image data, video data, and/or the like.

Figure 2:
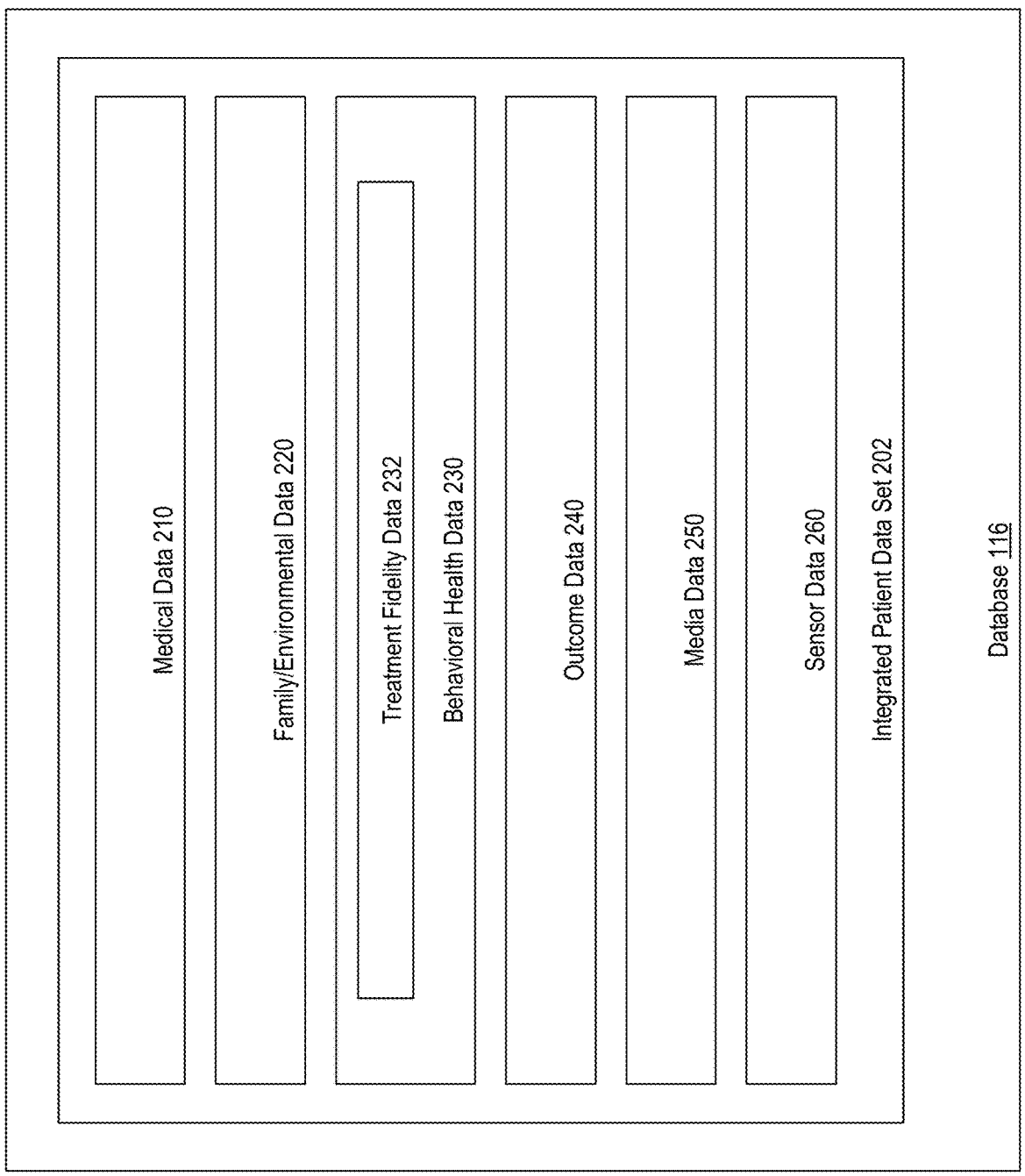
FIG. 2 illustrates an example database and data contained therein according to the various embodiments of the present disclosure.

FIG. 2 illustrates additional details including various data stored in the database 116. As shown in FIG. 2, the database 116 may include an integrated patient data set 202 comprising various types of data such as medical data 210, family and environmental data 220, behavioral health data 230, outcome data 240, media data 250, sensor data 260, and the like. By collecting and processing these data to generate a training data set, the system may develop various machine learning and/or AI models (as described in more detail below) that may improve a treatment plan, for example by enhancing program design and/or predicting outcomes more effectively.

The medical data 210 may encompass various subtypes of data. For example, the medical data may include medical history data, which could be information about various patients' past medical records, including diagnoses, treatments, comorbidities, medical procedures, conditions, parent/guardian reports, and/or the like. For example, this data may help various machine learning models identify patterns and correlations between a patient's medical background and their response to specific interventions.

Additionally or alternatively, medical data 210 may include diagnosis data, which may provide insights into the patient's current condition, such as the severity of a condition (e.g., a severity of autism spectrum) and/or any co-occurring medical issues. In case of autism diagnosis, the data may include standardized tests such as Autism Diagnostic Observation Schedule (ADOS) or Autism Diagnostic Interview-Revised (ADI-R). The diagnoses may be time-stamped to allow the system 110 to determine a change in diagnosis over time. In some examples, one or more machine learning models may use this information to tailor treatment recommendations or predictions based on a patient's unique diagnostic profile.

Additionally or alternatively, medical data 210 may include sleep patterns data, which could be gathered through wearable devices, sleep tracking apps, surveys, logs, etc. This data may offer valuable information about the patient's sleep duration, quality, and/or disruptions. In embodiments, this data may be time-stamped, thus enabling the models described herein to learn how changes in sleep patterns may or may not impact other variables, outcomes, or predictions, such as behavioral symptoms and/or treatment outcomes.

Additionally or alternatively, medical data 210 may include neuroimaging data (e.g., MRI, fMRI, or EEG scans), which may provide insights into patients' brain structure and function. In some examples, the models described herein may use this data to identify, for example, neural markers associated with condition severity, treatment response, and/or potential for behavioral shifts.

Additionally or alternatively, medical data 210 may include genetic information, which may be obtained through genetic testing and/or family history. For example, this data may be used by the models described herein to identify genetic factors that influence condition risk, presentation, and/or treatment response. By incorporating this data, the models may be able to better predict which patients are likely to benefit from certain interventions based on their genetic profile.

Additionally or alternatively, medical data 210 may include medications and supplements data, including adherence to dosing regimens, indicating medications and supplements taken at various times (e.g., the data may be time-stamped and/or include prescription information indicating changes in medication over time). This data may enable the models described herein to correlate a patients' medications or supplements to other outcomes data.

In embodiments, the family and environmental data 220 may include various types of data. For example, family guidance data may indicate various data provided by or to a family, such as treatment instructions provided to a family of a patient and/or information collected from the family such as level of support, involvement, and/or understanding. Additionally or alternatively, the family and environmental data may include cultural and linguistic factor data, such as the family's primary language, cultural background, and/or beliefs about a condition and its treatment. Additionally or alternatively, the family and environmental data may include family socioeconomic status data, such as data on income, education level, access to healthcare resources, etc. In embodiments, the models described herein may use various family and environmental data to learn how the various factors correlate to treatment adherence and/or effectiveness and/or how to better generate personalized treatment plans.

In embodiments, behavioral health data 230, which may include treatment fidelity data 232, may be particularly valuable for training the models described herein. In some embodiments, some or all of the behavioral health data may be weighted highly in a training data set and/or as inputs during inference. In embodiments, the behavioral health data may include behavioral observations data, which may be collected by caretakers and/or other treatment providers. This data may include detailed measurements and/or observations regarding patients' day-to-day functioning, challenges, and/or progress. For example, this data may include indicators of the frequency and/or severity of various symptoms (e.g., ASD symptoms such as social communication difficulties, repetitive behaviors, sensory sensitivities, etc.). In embodiments, the models described herein may use this data to detect patterns that may be useful to predict potential behavioral shifts, identify triggers for certain behaviors, and/or the like.

In embodiments, behavioral health data 230 may include reinforcement data, which may be information about the patient's response to different types of rewards and/or incentives (e.g., praise, toys, tokens, etc.). This data may be used by the models described herein to optimize treatment strategies, for predictive analytics, and/or the like. For example, this data may indicate that a patient responds well or poorly to certain types of reinforcement, which may tend to indicate treatment plan modification to incorporating more of that type of reinforcement into their treatment plan (e.g., at least in some situations and/or to respond to certain types of behaviors).

Additionally or alternatively, behavioral health data 230 may include social interactions data, which may be observations of the patient's interactions with peers, family members, and/or treatment providers. This data may indicate various measurements regarding social skills, challenges, and the like, and may be particularly useful in an ASD context.

Behavioral health data 230 may include treatment fidelity data 232, which may include various indicators of how closely treatment providers adhere to prescribed intervention protocols. In example embodiments, this data may be crucial for ensuring the integrity and effectiveness of a treatment plan. The treatment fidelity data may include assessments, observational data, supervisor/peer reviews of a treatment session that measure implementation adherence, and/or the like. In some cases, treatment fidelity data may itself include the outputs of machine learning and/or regression models, such as models that output various scores and/or other predictions that better measure various aspects of treatment fidelity and/or how to improve treatment fidelity. These scores and/or predictions are described in more detail below.

Treatment fidelity assessments may be provided by an assessor charged with assessing the treatment of a patient. For example, the assessor may observe a care provider (e.g., a Board-Certified Behavior Analyst ("BCBA") treating a patient with ASD) during treatment and generate data assessing the treatment fidelity. As another example, a BCBA may fill the role of assessor to observe a behavior technician providing care. Treatment fidelity data may include a wide variety of assessments of treatment fidelity, which are described in more detail in the following section. Each assessment may include various assessment questions and answers, which may be structured as checklists (e.g., indicating a particular assessment was passed/completed/positive or not), rating scales, and/or the like. Moreover, each question and answer may be tagged with various data indicating the type of assessment or assessment component.

Additionally or alternatively, behavioral health data 230 may include program design data, which may be information such as therapist session notes, treatment plans, and/or individualized education plans. The program design data may specify one or more specific goals, strategies, and/or activities that are included in patients' treatment plan. In embodiments, some or all of this data may be further processed (e.g., using generative AI models to categorize session notes) to generate more structured data that may be better used as inputs for a machine learning model. In this form, the data may be used by the various models described herein to optimize an intervention approach by correlating various aspects of the treatment plan to other variables and/or outcomes.

Additionally or alternatively, behavioral health data 230 may include environmental considerations data, which may include various indicators regarding conditions (and/or changes to conditions) in patients' various settings (e.g., home, school, community, etc.). In some cases and/or for some settings, this data may be automatically gathered by various sensors (e.g., noise sensors, temperature sensors, etc.) and time-stamped. Additionally or alternatively, the information may indicate, for example, a number of other individuals present, specific individuals that are present, etc. In embodiments, data indicating the presence of other individuals may be manually generated. Additionally or alternatively, the system 110 may analyze (e.g., using machine vision models, generative models, etc.) audio or video footage to detect the presence, number, and/or identity of other individuals, and/or to otherwise characterize a patients' environment. This data may be used by the various models described herein to identify environmental factors that may support or hinder treatment progress, correlate with certain behaviors, etc.

Additionally or alternatively, behavioral health data 230 may include generalization and maintenance data, which may be indicators of patients' ability to apply skills learned in treatment to new settings and/or maintain progress over time. This data may be indicative of long-term outcomes, and thus may be used for various models described herein for predictive analytics and/or other use cases that require analyzing whether treatment gains can be successfully generalized and/or maintained over time.

Additionally or alternatively, behavioral health data 230 may include parent or guardian feedback and/or participation data, which may include indicators of patients' families' feedback during treatment, participation in treatment, patient progress, perceptions of patient improvements, concerns or challenges, other observations, etc. In embodiments, the various models described herein may learn to correlate this data to outcome data to learn the impact of treatment approaches and/or how they align with data from the family.

The integrated dataset 202 may further include outcome data 240, which may include outcomes based on standardized assessments (e.g., Autism Diagnostic Observation Schedule (ADOS), Vineland Adaptive Behavior Scales, and/or Assessment of Basic Language and Learning Skills-Revised for ASD). Additionally or alternatively, the outcome data 240 may include any other data that may provide objective measures of patients' progress over time. In embodiments, the data may be timestamped and/or may indicate whether the assessment occurred pre- or post-treatment. This data may provide objective and standardized outcome data that may be used in several capacities, for example to evaluate the effectiveness of a treatment plan and/or to predict future outcomes based on changes in outcome data over time.

In some cases, outcome data may be fairly simple, such as one or more indications generated by a caregiver (e.g., at the end of a treatment session) of whether the sessions went well, whether a patient improved or regressed on one or more aspects, any challenges that arose during treatment, and/or the like.

Additionally or alternatively, outcome data 240 may include detailed summaries of the results of example treatments and/or associated assessments. These treatments and assessments may include, for example, behavior reduction programs that focus on reducing problematic behaviors and include techniques such as extinction procedures (e.g., planned ignoring, tangible extinction, escape extinction) and differential reinforcement procedures (DRO, DRI, DRH, DRA, DRL). Response cost procedures like token loss, time-out, and loss of privileges may also be used.

Treatments and assessments may also include skill acquisition programs that aim to teach new skills. These programs may include discrete trial training (DTT) with variations like massed, distributed, and expanded trial instruction, natural environment training (NET) using incidental teaching, mand model procedure, and time delay procedure, task analysis with forward chaining, backward chaining, and total task presentation, verbal behavior programs focusing on mand training (echoic-to-mand transfer, multiple mand training, spontaneous mand training), tact training (pure tacts, impure tacts, tact extensions), intraverbal training (textual intraverbals, conversational intraverbals, intraverbal chains), and functional communication training (FCT) for replacing challenging behaviors.

Assessments may further include preference assessments, which help determine an individual's preferences. These may include single stimulus preference assessment using approach method and duration method, paired stimulus preference assessment with simultaneous and sequential presentation, multiple stimulus assessment using multiple stimulus without replacement (MSWO) and multiple stimulus with replacement (MSW), free operant preference assessment with contrived and naturalistic free operant methods.

Assessments may also include metrics for skill acquisition and professionalism for evaluating the performance of behavior analysts. Outcome data 240 may summarize the results of any or all of these procedures, as well as other outcomes. For example, outcome data may indicate whether a patient achieved a certain goal, did well on a certain procedure, learned a new skill, reduced a behavior, and/or the like.

The dataset 202 may further media data 250 (e.g., audio or video of a treatment) and/or sensor data 260, which are discussed in more detail below.

In embodiments, the database 116 may correlate these diverse types of data into an integrated patient dataset 202, tagging each by patient, to create a large data pool involving many numbers of patients. Thus, for example, each patient in the database 116 may be associated with one or more of the various medical data 210, family and environmental data 220, behavioral health data 230, outcome data 240, media data 250, and/or sensor data 260 described above.

In embodiments, the database 116 may store the various data types described above in a structured format that facilitates efficient retrieval and analysis, particularly for machine learning applications. For example, each item of data may be associated with a unique patient identifier. To protect patient privacy, the unique patient identifier may be an anonymized identifier that is not directly linked to personally identifiable information (PII) in the database 116.

Some or all of the data in the database 116 (e.g., any data that varies over time) may be associated with timestamps or other relevant timing data. The timing data beneficially captures the temporal nature of certain data, which may be relevant for identifying trends/patterns, predicting future outcomes, and/or evaluating the impact of interventions over time.

The various data in the database 116 may be gathered from a variety of sources, such as medical records, patient surveys, IoT devices, treatment provider observations, and/ or the like, as described in more detail below. To accommodate the diversity of data sources, the database 116 may employ flexible schemas and/or use semi-structured data formats like JSON.

Figure 3:
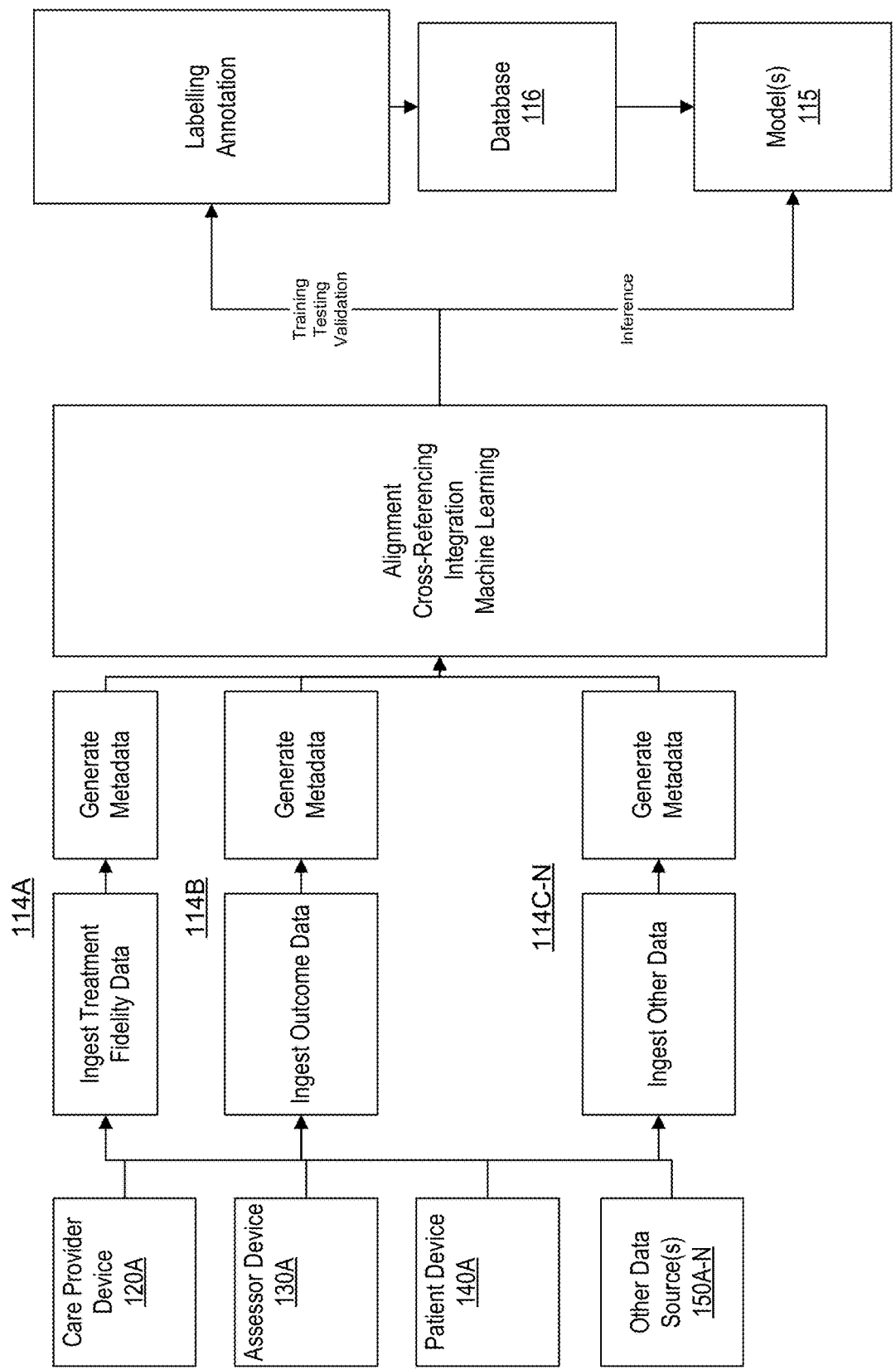
FIG. 3 illustrates an example data intake process as described within the present disclosure.

In some embodiments, the raw data collected from various sources may undergo preprocessing or transformation before being stored in the database 116, as described in more detail with respect to FIG. 3. The preprocessing may involve using AI techniques like natural language processing (NLP) or generative language models (e.g., LLMs) to generate structured data from unstructured text or other data, such as images or videos. For example, the system may use a generative model to create objective/structured metrics based on subjective observations provided by treatment providers, family members, etc.

To facilitate machine learning, the database 116 may be organized and stored in structures that are optimized for model training and evaluation. For example, the database 116 may be partitioned into separate tables or collections for training data, validation data, and/or test data.

Treatment Fidelity Assessments

The system 110 may receive and/or generate a variety of treatment fidelity assessments, which are described in detail in this section. Various subsets of the following assessments may be used for each patient, care provider, and/or treatment plan. The specific assessments below may be used to generate various treatment fidelity scores in an ASD context. For example, a clinical score may indicate whether a care provider is accurately providing clinical care (e.g., accurately following clinical procedures, responding to patients in clinically prescribed ways, etc.). An environmental score may indicate whether any environmental factors are inhibiting treatment effectiveness (e.g., by interfering with a care provider's effectiveness). A professionalism score may indicate whether the care provider is behaving in a professional way (e.g., showing up on time, responding to feedback, etc.). However, other assessments may be used in other contexts (e.g., for treating different conditions) and/or for generating other scores. For example, a permanent product review score may indicate the quality and effectiveness of a treatment based on the tangible materials or data generated during the treatment process, rather than through direct observation of the patient or care provider. For example, the ASD context, permanent products may include session notes (e.g., taken by a care provider), data collection sheets (e.g., for recording patient progress on tasks), work samples (e.g., as generated by a patient), etc. Additional materials that may be used as permanent products include the assessments described below, such as the Clinical Audit Assessment, the Session Note Treatment Integrity Assessment, etc. It should be noted that although these assessments are described below as influencing a clinical score and a professionalism score respectively, they may also (or alternative) be used to generate other scores such as a permanent product review score.

Professionalism Metrics: This assessment may be completed by an assessor and may assess a care provider's performance in various professional areas such as assertiveness, time management, business etiquette, ethics, leadership, interpersonal skills, problem solving, temperament, and/or competence. This assessment may be used to generate a professional score for a care provider.

Behavioral Skills Training Assessment: This assessment may be used when a care provider is training using Behavioral Skills Training (BST). For example, a care provider (e.g., BCBA) may complete a checklist with a behavior technician who is using BST to teach a client social skills. It could also be used by an assessor to assess a care provider (e.g., BCBA) training with a behavior technician. The behavior skills training may include providing instructions, modeling, rehearsing, and providing feedback to teach a new behavior. This assessment may be used to generate a clinical score.

Behaviors Targeted for Reduction Assessment: This assessment may be used to assess behavior technician use of behavior reduction procedures. It may be used throughout a session and/or may include a component that only triggers if/when a patient engages in a targeted behavior. In these embodiments, after a patient engages in a targeted behavior, the behavior technician's response to the targeted behavior may be assessed. This assessment may be used to generate a clinical score.

Chaining Assessment: This assessment may be used for any programs in which forward, backward, or total task chaining is used (e.g., chaining together manageable steps to teach a patient to perform complex actions more independently). This assessment may be used to generate a clinical score.

Clinical Audit Assessment: This assessment may be completed by an assessor of a care provider (e.g., BCBA). The assessment measures how well the care provider is managing their cases from a clinical perspective in terms of skill acquisition and/or behavior reduction programming. In some cases, this assessment can also be used as a self-assessment for care providers to measure how well they are managing their case. This assessment may be used to generate a clinical score.

Denied Access Assessment: This assessment may measure behavior technician implementation of a denied access procedure (e.g., a procedure to assist a patient in dealing with a denial of an item or activity that cannot be provided). This assessment may be used to generate a clinical score.

Differential Reinforcement of Behavior Assessment(s): These assessments may assess behavior technician use of various differential reinforcement procedures, such as a differential reinforcement of alternative behavior procedure, a differential reinforcement of high rates of behavior procedure, a differential reinforcement of incompatible behavior procedure, a differential reinforcement of low rates of behavior procedure, and/or a differential reinforcement of other/zero behavior procedure. The assessment(s) may be used throughout a session and/or may include a component that only triggers if/when a patient engages in a targeted behavior. In these embodiments, after a patient engages in a targeted behavior, the behavior technician's response to the targeted behavior may be assessed. These assessments may be used to generate a clinical score.

Discrete Trial Teaching Without Stimuli Assessment: This assessment may measure behavior technician implementation of a discrete trial without stimuli procedure (e.g., a procedure to present a specific instruction or task to a patient without using any additional visual, auditory, or physical prompts to test whether the patient can respond to the instruction independently). This assessment may be used to generate a clinical score.

Feedback Reception Assessment: This assessment may measure how well a care provider responds to feedback they receive. This assessment may be used to generate a professionalism score.

Free Operant Assessment: This assessment may measure behavior technician implementation of a free operant preference assessment procedure (e.g., a procedure for allowing a patient to freely interact with various stimuli to discover patient preferences). This assessment may be used to generate a clinical score.

Functional Communication Training Assessment: This assessment may measure behavior technician implementation of a functional communication training program (e.g., a procedure to assist a patient to express their needs, wants, or feelings through appropriate communication methods). This assessment may be used to generate a clinical score.

Instructional Control Treatment Integrity Assessment: This assessment may measure behavior technician instructional control integrity (e.g., measures of a caretaker's consistency and/or accuracy for the delivery of instructions and following of procedures). This assessment may be used to generate a clinical score.

Match to Sample Assessment: This assessment may measure behavior technician implementation of a match to sample procedure (e.g., a procedure to assist a patient to match a sample stimulus to an identical or similar comparison stimulus). This assessment may be used to generate a clinical score.

Motor Play Assessment: This assessment may measure behavior technician implementation of a motor play procedure (e.g., a procedure to assist a patient with structured play activities that focus on physical movements). This assessment may be used to generate a clinical score.

MSWO Preference Assessment: This assessment may measure behavior technician implementation of a multiple stimulus without replacement (MSWO) preference assessment procedure (e.g., a procedure used to identify a patient's preferences for various stimuli). This assessment may be used to generate a clinical score.

Natural Environment Training Assessment: This assessment may measure behavior technician implementation of a natural environment training procedure (e.g., a procedure to teach a patient skills in their natural environment). This assessment may be used to generate a clinical score.

Noncontingent Reinforcement Assessment: This assessment may measure behavior technician use of noncontingent reinforcement (e.g., a behavior management strategy to reduce challenging behaviors and increase appropriate behaviors). This assessment may be used to generate a clinical score.

Paired Stimulus Preference Assessment: This assessment may measure behavior technician implementation of a paired stimulus preference assessment procedure (e.g., a procedure used to identify a patient's preferences by presenting them with pairs of stimuli and asking them to choose one). This assessment may be used to generate a clinical score.

Pairing Treatment Integrity Assessment: This assessment may measure behavior technician use of pairing (e.g., a process of establishing a positive and reinforcing relationship between the care provider and the patient). This assessment may be used to generate a clinical score.

Pretend Play Assessment: This assessment may measure behavior technician implementation of a pretend play procedure (e.g., a procedure to assist a patient to develop symbolic play skills). This assessment may be used to generate a clinical score.

Providing Effective Feedback Assessment: This assessment may measure how a care provider provides feedback. This assessment may be used to generate a professional score.

Reinforcer Relinquishment Assessment: This assessment may measure behavior technician implementation of a reinforcement relinquishment procedure (e.g., a procedure to teach a patient to give up a reinforcer when asked to do so). This assessment may be used to generate a clinical score.

Session Environmental Barriers Assessment: This assessment may measure any environmental barriers that impact care provider performance. This assessment may be used to generate an environmental score.

Session Note Treatment Integrity Assessment: This assessment may measure behavior technician completion of session notes. This assessment may be used to generate a professional score.

Session Professionalism Assessment: This assessment may measure behavior technician professionalism. This assessment may be used to generate a professional score.

Session Intensity Assessment: This assessment may measure the intensity of a session by measuring 1) a ratio of skill acquisition to maintenance trials and/or 2) a ratio of verbal operants or demands per time sample. This assessment may be used to generate a clinical score.

Skill Acquisition Program Treatment Integrity Assessment: This assessment may measure how a care provider (e.g., BCBA) is designing skill acquisition programs. This assessment may be used to generate a clinical score.

Social Skills Assessment: This assessment may measure behavior technician implementation of a social skills procedure (e.g., a procedure to assist a patient in learning social skills). This assessment may be used to generate a clinical score.

Toilet Training Treatment Integrity Assessment: This assessment may measure behavior technician implementation of a toilet training procedure. This assessment may be used to generate a clinical score.

Tolerance Shaping Assessment: This assessment may measure behavior technician implementation of a tolerance shaping procedure (e.g., a procedure to assist a patient increase their tolerance for aversive or less preferred stimuli). This assessment may be used to generate a clinical score.

Transitions Assessment: This assessment may measure behavior technician implementation of a transitioning procedure (e.g., a procedure to assist a patient's ability to move smoothly from one activity or setting to another). This assessment may be used to generate a clinical score.

Treatment Plan Assessment: This assessment may measure compliance of a treatment plan with insurance requirements. This assessment may be used to generate a clinical score.

Verbal Behavior Echoics Assessment: This assessment may measure behavior technician implementation of an echoic procedure (e.g., a procedure to assist a patient to develop vocal imitation skills). This assessment may be used to generate a clinical score.

Verbal Behavior Intraverbals Assessment: This assessment may measure behavior technician implementation of an intraverbal procedure (e.g., a procedure to teach conversational skills and the ability to respond appropriately to verbal stimuli). This assessment may be used to generate a clinical score.

Verbal Behavior Manding Assessment: This assessment may measure behavior technician implementation of a manding procedure (e.g., a procedure to assist a patient to make requests or express their wants and needs). This assessment may be used to generate a clinical score.

Verbal Behavior Tacting Assessment: This assessment may measure behavior technician implementation of a tacting procedure (e.g., a procedure to assist a patient to label or describe objects, actions, or events in their environment). This assessment may be used to generate a clinical score.

For each type of assessment, multiple values may be recorded. In some cases, the values may be either positive or negative (e.g., indicating that an aspect was performed correctly or not). Additionally or alternatively, errors may be tagged with indicators of the type of error. For example, if a care provider provides an incorrect prompt during a procedure, the error may be tagged as a "prompt error." If a care provider misses a prompt, the error may be tagged as an "omission error." If a care provider does not properly reinforce a positive behavior, the error may be a "reinforcement error." Other types of errors may also be logged and tagged.

As an example set of values for a particular assessment, a behavioral skills assessment may include indicators of whether a care provider 1) successfully paired with a patient, 2) provided the patient with instructions to complete a target behavior, 3) modeled how to engage in the target behavior, 4) modeled the target behavior accurately, 5) provided an opportunity for the patient to practice the behavior, 6) collected data on the treatment integrity, 7) collected accurate data on the treatment integrity, 8) provided immediate feedback after the patient practiced the behavior, 9) faded feedback according to a plan, 10) answered a patient's questions, and 11) adhered to compassionate care principles. Similarly, other assessments may include multi-factor evaluations of treatment fidelity.

Example Methods

FIG. 3 shows an intake method for receiving various types of data, processing the data using data pipelines, and preparing the data for use by the system 110 (e.g., for training, testing, validation, and/or inference). The method of FIG. 3 may be used to generate an integrated data set 202 for storage in the database 116. The integrated data set 202 may be compiled and annotated using the method of FIG. 3 prior to training and testing. Then, after one or more trained models have been developed, additional data may be received and processed using some or all of the steps of method of FIG. 3 prior to ingestion by a model for inference (e.g., generation of any of the predictions/outcomes described herein).

As shown in FIG. 3, data may be collected from various devices, including care provider devices, assessor devices, patient devices, and other data sources, which may include devices associated with family members, third party databases, sensors, IoT devices, and/or other sources of various data including medical records, environmental data sources, behavioral data sources, and/or the like.

FIG. 3 further depicts example data "pipelines" 114 that may be configured to ingest different types of data. A first data pipeline 114A may ingest treatment fidelity data, which is described above. A second data pipeline 114B may ingest patient outcome data (e.g., data indicating treatment outcomes, such as patient tests and/or surveys indicating whether a patient improved or not, whether a condition increased or decreased in severity, and/or the like. Additional data pipelines 114C-N may ingest other data, which may include any of the data described as being within the integrated data set 202 above. In practice, any number of data pipelines may be used for various types of data.

The first pipeline 114A may receive treatment fidelity data from a care provider device 120A, assessor device 130A, and/or some other device. Using the pipeline 114A, the system 110 receives the treatment fidelity data and generates relevant metadata, which may include information describing the treatment fidelity data, such as a format of the data, a provenance of the data, a patient identifier, timestamp, care provider identity, and other such relevant details. In some cases, if the treatment fidelity data is missing information necessary to generate the metadata, the system 110 may prompt the source device for additional information (e.g., via a user interface). Additionally or alternatively, the system 110 may be able to automatically extract and/or format metadata from the treatment fidelity data itself.

The second data pipeline 114B may receive patient outcome data. This data may be received from the care provider device, patient device, a device associated with family members, and/or other relevant data sources. Outcome data may include survey results, diagnoses, or exam results. An illustrated third set of data pipelines 114C-N may receive other types of data, such as behavioral data, environmental data, medical data, etc. The system 110 may use each pipeline 114 to generate metadata tailored to the specific type of outcome data being processed. For example, the system 110 may generate metadata that specifies a data format and/or provenance, indicates one or more units of measure, indicates a timing cadence, indicates whether the data is unstructured or not, includes one or more patient identifiers, and/or the like.

After being processed through the respective data pipelines, the system 110 may perform one or more further pre-processing functions such as alignment, cross-referencing, integration, and/or other such functions for generating an integrated dataset. The pre-processing may prepare the data for storage in the integrated patient dataset 202 of the database 116 and/or prepare the data for inference by conducting data cleanup, sanity checks, and/or other operations. In some cases, the system 110 may perform one or more alignment operations such as converting data to a standardized format (e.g., standardizing date and time formats), grouping data, mapping data from different sources to a common schema or data model, resolving any discrepancies or conflicts between data from different sources, and/or the like. Additionally or alternatively, the system 110 may perform one or more cross-referencing operations including linking data from different sources that refer to the same patient, care provider, and/or event, identifying and linking/merging duplicate records, establishing relationships between different data entities (e.g., linking a patient's medical history to their treatment outcomes), and/or the like. Additionally or alternatively, the system 110 may perform one or more integration operations including combining data from various sources into the same dataset, aggregating or summarizing data at different levels of granularity (e.g., creating daily, weekly, or monthly summaries of patient data), enriching the data with additional context or derived attributes (e.g., calculating a patient's age based on their date of birth), and/or the like.

In some cases, the pre-processing may further include machine learning operations, such as using trained model(s) 115 to transform data and/or generate additional data for storage in the integrated data set based on one or more inputs from the various pipelines 114. For example, the system 110 may use generative AI models to convert subjective or free-form textual data into objective and/or structured data that may include scores or metrics that are more suitable for downstream machine learning tasks.

For data that will be used to train, test, or validate machine learning models, the system 110 may perform an additional labeling and/or annotation step. In embodiments, labeling may include adding labels, tags, or other metadata to the data to support supervised learning tasks. The specific labeling process may vary depending on the type of data and the target variable being predicted. Various target variables are described in more detail below with respect to the various models 115. In some cases, outcome data 240 may be used to label data (e.g., if a particular outcome is a target variable for a model 115).

In embodiment, the system 110 may also annotate the labeled data. For example, annotation may include generating data that is indicative of changes to certain data over time (e.g., by including a delta value indicating an amount by which a value has changed, and/or including one or more previous values for the data value) and/or other supplemental information. Additionally, the system 110 may annotate audio data (e.g., audio recorded during a treatment session) with text data generated from the audio data using speech to text algorithms. As another example, the system 110 may annotate video data (e.g., video of a treatment session) with data indicating when certain procedures were performed (e.g., based on timestamped assessment data), when certain patient behaviors were detected (e.g., based on video analysis of patient behavior), and/or the like. As another example, a treatment could be annotated with the identity of the care provider (e.g., such that patterns arising from changing care providers can be detected), an indicator of whether a care provider changed since the last treatment, etc. Accordingly, the system 110 may store the processed and labeled/annotated data in the database 116. If the data is stored in the integrated patient dataset, the system 110 may anonymize the data to remove any personally identifiable information (PII). For example, data used for training, testing, and validation may be stored in the integrated patient data set 202 of the database 116.

In some cases, the system 110 may receive data that may be used for inference. In these cases, the system 110 may optionally bypass storage and be fed into one or more the machine learning models 115 (e.g., using the methods of FIG. 4). However, in these cases, the input data and/or prediction data may optionally be stored within the database 116.

In embodiments, the intake method of FIG. 3 may occur at the time of an assessment. For example, during treatment of a patient, treatment fidelity data (e.g., as described above) may be collected by the system 110 and processed (e.g., used for inference and/or added to the integrated patient data set for training/testing/validation). Other data (e.g., sensor data, other patient data, etc.) may be collected by the system 110 at the same time and/or at a different time.

In embodiments, the intake method of FIG. 3 may be executed repeatedly for a single patient. For example, after every assessment involving a patient, new and/or updated treatment fidelity data and/or other types of data may be fed into the system 110. In embodiments, the new and/or updated data for a patient may be combined with existing data for the patient (e.g., from the database 116) to generate inputs to the models 115 for inference. Additionally or alternatively, other patient data (e.g., from similar patients within the database 116) may, in some cases, be used for inference.

In some embodiments, such as the real time monitoring system described in more detail below, the intake method of FIG. 3 may be executed frequently and/or in a loop. For example, data may be streamed into the system 110, processed (e.g., to determine trigger events), and used for inference on a repeating and/or ongoing basis.

In some cases, the intake method of FIG. 3 may be refined over time. For example, the inference process described below with respect to FIG. 4 may use a variety of models 115 to perform various predictions. These models may be analyzed to determine which data inputs provided the most and/or least impact. In some cases, it may be determined that certain inputs are merely noise and may be disregarded for some or all analyses. In these cases, the intake method of FIG. 3 may be modified to remove the intake of the corresponding data (e.g., which may involve no longer collecting data and/or no longer requesting the collection of data). Additionally or alternatively, it may be determined that certain inputs have a high impact on one or more outcomes. In some of these cases, the intake method of FIG. 3 may be updated to collect more of the most important type of data (e.g., more frequently, in more detail), etc. In embodiments, the system 110 may perform these functions automatically and/or under the control of one or more operators. For example, the system 110 may automatically analyze models to determine which types of inputs have high or low impact on outcome variables and adjust the intake method accordingly.

Additionally or alternatively, the system 110 may refine the inputs that are provided to the models 115 based on determinations of which inputs are most or least impactful. For example, some of the assessments of treatment fidelity may be more important than others for determining treatment fidelity score(s) or other outcomes. If certain assessments have little or no impact on an outcome, the system 110 may avoid providing those inputs to the model 115 (e.g., to speed up inference).

Figure 4:
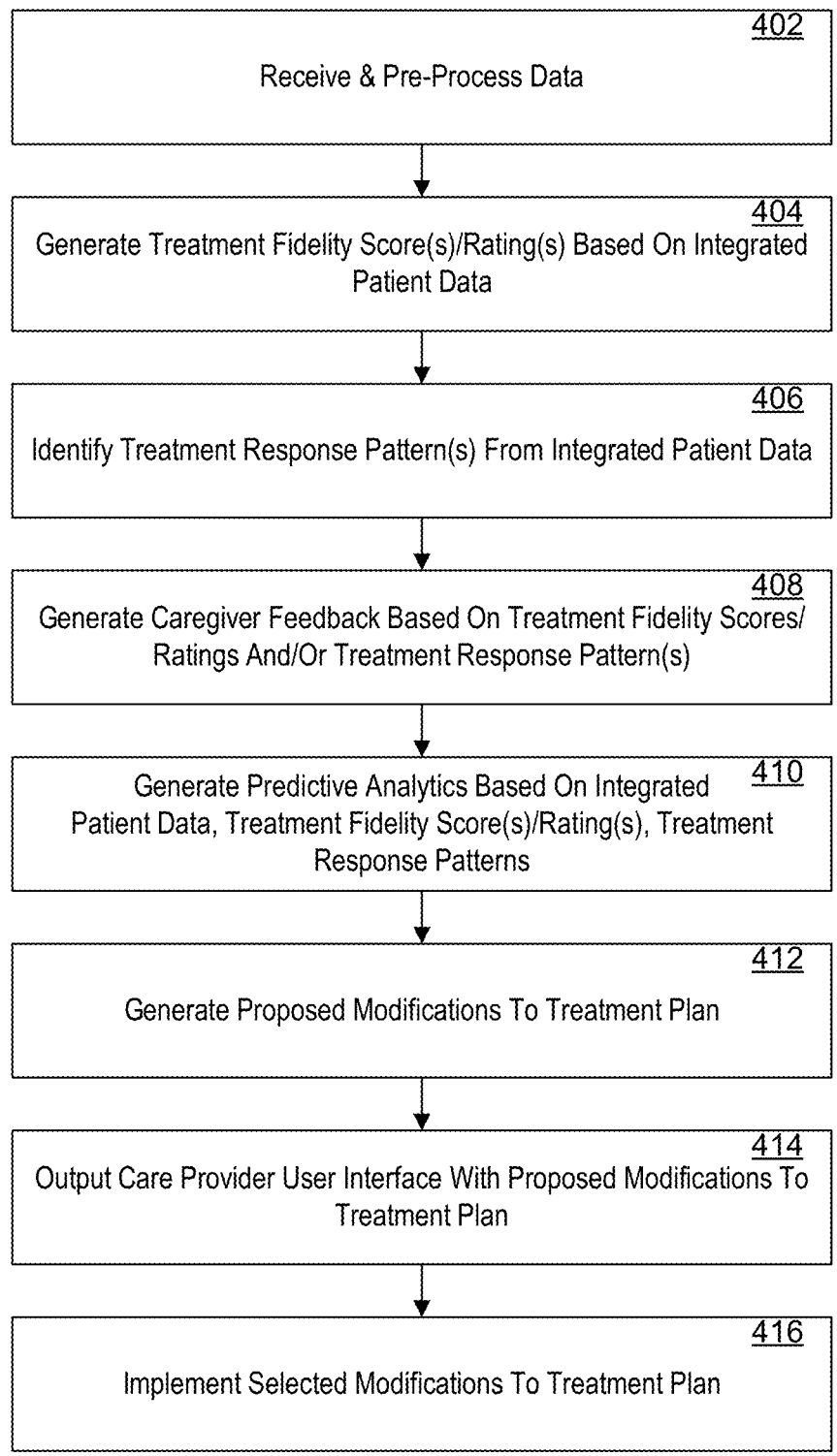
FIG. 4 illustrates an example inference process as described within the present disclosure.

FIG. 4 illustrates an example inference method for generating various predictions, feedback, and/or treatment plan modifications based on various patient data. In this context, inference includes the process of feeding data into a trained model 115 to generate the various predictions/scores/ratings described below. The inference process shown in FIG. 4 may be triggered by the availability of new data for a patient, such as data from a recent assessment, treatment session, or standardized test. The system 110 may receive/process this new data and combine it with any relevant existing data about the patient. The system 110 may then combine the data and feed it into the trained models to generate the treatment fidelity scores and ratings, which serve as indicators of treatment effectiveness and may help identify areas for improvement.

At step 402, the system 110 receives and pre-processes data for inference. This step may be implemented using the data intake and preparation process described in FIG. 3, where different types of data (e.g., treatment fidelity data, patient outcome data, behavioral data, environmental data, medical data, etc.) are ingested through various data pipelines 114, processed, and (in some cases) stored in the integrated patient dataset 202 of the database 116. In some cases, the data used for inference may include both newly received data and historical data previously stored in the database 116. For example, when the system 110 receives new patient data (e.g., during or after an assessment or other treatment), the system 110 may combine the new patient data with the patient's previous data to generate inferences based on a more comprehensive patient history. In some cases, the system may generate inputs by combining current data with a subset of past data. For example, the system 110 may generate inputs based on data collected during the last week, month, 90-day period, etc. In some cases, the system 110 may generate inputs that are derivative of large amounts of time-specific data (e.g., running averages). The system 110 may generate and provide multiple of these figures (e.g., a past week average, a past month average, and a past year average, etc.) as inputs for any of the models 115 described below.

At step 404, the system 110 generates one or more treatment fidelity scores or ratings based on the integrated patient data and optionally, cross-patient data. The treatment fidelity scores may include various metrics such as a clinical score, professionalism score, environmental score, and/or the like as described in the treatment fidelity data section above. The system 110 may generate these scores based on the detailed treatment fidelity data (e.g., detailed assessment answers, logged errors, etc.) and may also incorporate other relevant data to provide a more comprehensive assessment of treatment effectiveness. As one example, the various sensor data and/or environmental data described above may be added to treatment fidelity data as inputs to a model 115 to increase the comprehensiveness of an environmental score.

The treatment fidelity scores or ratings may take different forms, such as numerical scores within a specific range (e.g., 0-100), categories, tags, and/or the like. For instance, a clinical score might represent a care provider's treatment effectiveness on a scale from 0 to 100. Additionally or alternatively, an environmental score could include tags indicating specific environmental stressors or triggers that impacted a patient during a particular treatment session. In some cases, several scores may be generated for different time periods. For example, the system 110 may generate a treatment-specific clinical score for the most recent treatment and/or one or more clinical scores based on data for the last N number of treatments (e.g., where N may a configurable number received and stored by the system 110), all treatments within a certain time period (e.g., the past 3 months), and/or the like. Accordingly, the system 110 may generate short and long-term scores (which may be overlapping or not).

To generate the scores, the system 110 employs models 115 that are trained on the integrated patient dataset 202. The training process may involve various techniques to develop high quality models 115 that generate scores based on nuances and patterns within the data 202. In one example approach, the system 110 may use a simple model (e.g., based on algebraic equations or regression) to generate initial scores to label a training data set, and then develop a better model 115 (e.g., a neural network-based model using machine learning) that uses the labeled training data set as well as other data (e.g., the data described above) to determine particular patterns that are indicative of higher treatment effectiveness or not. As one example of these patterns, consider two scenarios: 1) a clinical score based on a 10-question survey, where the first three questions have negative responses, and the last seven have positive ones and 2) a clinical score where the first seven questions have positive responses and the final three have negative ones. A basic model might assign a score of 70/100 to both scenarios, but a more advanced model could be trained (e.g., using other data that is indicative of treatment effectiveness increasing over time) to recognize the first pattern (i.e., initial challenges followed by improvement) as indicating higher treatment fidelity than the second pattern (i.e., regression over time).

Additionally, the system 110 may include a separate model that correlates treatment fidelity scores (e.g., generated using the model 115 described above that generates treatment fidelity scores) and other data to outcome data (which may be the training label for training this model). This model may be referred to herein as an outcome prediction model 115. After training the outcome prediction model 115, the system 110 may use the outcome prediction model 115 to determine the ideal treatment fidelity scores for different circumstances (e.g., based on the environmental data and/or other data). Thus, the system 110 may learn to optimize the treatment fidelity scores in various situations, which in turn may enable the system 110 to improve the training of the model 115 that predicts treatment fidelity scores.

The system 110 may train and use different models 115 for each type of treatment fidelity score, such as separate models for clinical scores, environmental scores, professionalism scores, etc. These models can be trained using various data as described above. Each model 115 may output one score or a series of scores that measure different aspects of treatment fidelity.

In embodiments, the system 110 may store the generated treatment fidelity scores in the integrated patient data set 202 such that they are associated with a particular patient, particular treatment, etc. In other words, the treatment fidelity scores may measure treatment fidelity within a certain context. The system 110 may use this contextual relationship to optimize treatment plans in several ways. For example, some care providers may be better at certain procedures, may work better with certain types of patients, etc. The system 110 may detect these correlations using various pattern detection methods (as described in more detail below) and/or simply by generating average scores for certain contexts. For example, the system 110 may generate an average treatment fidelity score for a care provider for a certain procedure by averaging all of the treatment fidelity scores associated with the care provider providing that procedure. Similarly, if clusters of similar patients are detected, the system 110 may generate average treatment fidelity scores for the cluster of patients by averaging the treatment fidelity scores for the care provider when providing care to one of the patients within the cluster of patients. Accordingly, the system 110 may generate treatment fidelity scores that are event-specific as well as averages that may measure a care provider's skills in certain contexts. Similarly, the system 110 may monitor the change in treatment fidelity scores over time to detect changes in performance by a care provider, determine the cause of the changes (e.g., a deterioration of performance vs. the care provider being assigned different types of patients) and thereby improve responses to the changes.

In embodiments, the treatment fidelity scores generated at step 404 may be used to trigger one or more additional steps of the method of FIG. 4. For example, if the treatment fidelity scores (e.g., for a certain session) are below a certain threshold (e.g., a threshold numerical score), the system 110 may determine that certain aspects of the treatment plan are not operating optimally and accordingly execute one or more of the additional steps below (e.g., to modify a treatment plan based on the low treatment fidelity), but may skip the below steps if the treatment fidelity score(s) have not changed and/or remain high. For example, if a clinical score falls below a threshold, the system 110 may determine that a treatment plan is not optimized. As another example, if an environmental score falls below a threshold, the system 110 may determine that the environment of the patient is not optimized. Additionally or alternatively, the following steps may occur whenever the system 110 receives new data (e.g., for a new assessment).

At step 406, the system 110 identifies treatment response patterns from the integrated patient data. These patterns can be diverse and unexpected due to individual variance among patients (especially in contexts where patients may have difficulty communicating needs such as ASD, and therefore the patterns may be difficult to discern), and the system 110 may use large data sets and flexible learning techniques in order to allow the models 115 to discover group-based and/or individualized patterns. The treatment response patterns may be derived from various sources within the integrated patient data set 202. For example, the models 115 may be trained such that they identify patterns from similar patients in the training data who responded in certain ways to specific treatments. Alternatively, the patterns may be identified based on recurring events or trends within an individual patient's assessment history, although the amount of data available for a single patient may be limited compared to the entire integrated dataset.

The types of patterns identified by the models may be based on correlations between various absolute values, changes in values, and/or other first order, second order, or other changes in data. As a simple example, the trained models 115 may discover that patients with certain biometric data patterns (e.g., temperature, heart rate, or sleep patterns) captured by wearable devices respond better or worse to particular treatment approaches. In another example, the models 115 may discover that changes in a care provider (e.g., the fact that a care provider identity value has changed recently for a patient) or environment (e.g., relative changes in temperature during a treatment session) correlate to reduced outcomes, increased stress levels, greater errors in treatment fidelity, etc. As another example, the models 115 may uncover patient preferences or characteristics that have not been explicitly recognized by care providers but are predictive of treatment response. These patterns may be detectable via machine learning processes that train specific types of models 115 using large data sets. In some cases, the patterns may not be patient-specific, but instead may be provider-specific, treatment plan-specific, procedure-specific, etc.

The system 110 may employ various machine learning techniques to generate specific models 115 that may detect treatment response patterns. In some cases, the system 110 may use generative AI models, such as variational autoencoders (VAEs) or generative adversarial networks (GANs), which may be capable of learning underlying structure and patterns within datasets. The system 110 may train these models using the integrated patient dataset 202 to learn a compressed representation of the data that captures salient features and patterns. For generative models like VAEs or GANs, the model 115 outputs may be a set of latent variables and/or a compressed representation of the input data that encodes relevant patterns. One benefit of these types of models 115 is that the outputs can be further analyzed or visualized to identify specific patterns and/or clusters of patients with similar treatment response profiles. The system 110 may take advantage of these qualities, for example by generating user interfaces (e.g., for caretakers) that illustrate the analyses and/or include visualizations of the patterns/clusters for further analysis.

Additionally or alternatively, the system 110 may train deep learning models, such as convolutional neural networks (CNNs) or recurrent neural networks (RNNs). This type of model may be effective at processing structured data like time series or sequences. Thus, the system 110 may train CNN and/or RNN models 115 to predict treatment outcomes based on various input features, such as patient characteristics, treatment fidelity scores, and/or other relevant data as described above. During the training process, the models 115 learn to identify patterns and relationships that are predictive of treatment response. In these embodiments, the outputs of a model 115 may be a probability distribution over different treatment outcomes and/or a set of scores indicating the likelihood of various responses. Accordingly, the system 110 may use these outputs to identify patients who are more likely to respond positively or negatively to certain treatments based on their individual characteristics and/or identified patterns.

In some embodiments, the system 110 may collect a detailed patient-specific data set that may include, for example, sensor data from real-time and/or high-bandwidth sensors, such as IoT devices that may capture real-time patient data (e.g., biometric data), video cameras that may capture audio/video of a session, detailed transcripts of a sessions generated by transcription software, and/or the like. This detailed patient-specific data set may allow the system 110 to detect highly individualized patterns that may indicate, for example, correlations between various treatment fidelity factors (e.g., environmental factors, care provider performance factors, etc.) and patient factors (e.g., stress levels, outcome data indicating treatment effectiveness, etc.). The system 110 may detect (e.g., using the various techniques and/or models described above) these individualized response patterns and provide individualized modifications to a treatment plan, as discussed in more detail below. Moreover, because the volume of data for a patient may grow rapidly over time, the system 110 may be able to iteratively improve a treatment plan over time as more data is collected.

At step 408, the system 110 may generate care provider feedback based on the treatment fidelity scores or ratings and/or any identified treatment response patterns. This feedback may provide actionable insights to the care provider to help them improve the care they provide to the specific patient and/or potentially other patients as well. The system 110 may generate care provider feedback in various forms that can be tailored to a specific patient and/or treatment context. For example, if the treatment fidelity scores indicate that the care provider is not adhering to the prescribed treatment protocol, the system 110 may generate feedback that may include reminders or suggestions for improving fidelity. As a specific example, if environmental scores suggest that certain factors (e.g., noise levels or distractions) are impacting treatment effectiveness, the generated feedback may recommend strategies for mitigating those issues. In some cases, this feedback may be generated and provided to the care provider in real time, as described in more detail below.

The system 110 may also use the identified treatment response patterns to generate care provider feedback. As a simple example, if the models 115 detect that the patient responds better to certain types of reinforcement or instruction, the feedback might suggest incorporating more of those elements into the treatment plan. As another example, the patterns may indicate that the patient is more engaged or responsive during certain times of day or in specific settings, and therefore the feedback could recommend scheduling treatments accordingly. The system 110 may also simply summarize and/or visualize other more complex patterns for consideration by the care provider.

To generate care provider feedback, the system 110 may leverage natural language processing (NLP) techniques, such as language models (e.g., LLMs) or other text generation algorithms. In some cases, these models can be trained (e.g., using fine-tuning techniques) on a corpus of training data that includes inputs specifying treatment fidelity data and/or treatment response patterns (e.g., in the format output by the various models described above) and output that include expert-generated feedback and/or treatment recommendations. During inference (e.g., at step 408), the system 110 may then input the treatment fidelity data and/or treatment response pattern data for a patient into the relevant trained and/or fine-tuned models 115 (which may take treatment fidelity scores, response patterns, and/or other relevant data as inputs) to generate personalized feedback messages for display to care providers.

In addition to text-based feedback, the system 110 may generate visual or multimedia feedback and provide it to the care provider. For example, the system 110 may generate graphs or charts showing the patient's progress over time (e.g., by generating graphs/charts based on patient outcome data) in order to highlight areas of improvement or concern. The feedback may also include video demonstrations of specific treatment techniques or strategies that have been effective for similar patients. In embodiments, relevant videos may be selected from a corpus of videos and/or may be generated on-the-fly by the system 110 (e.g., using local or remote generative AI models).

The system 110 may deliver care provider feedback via a user interface 111, which may be configured to deliver information through one or more channels, such as a web-based dashboard, mobile app notifications, email reports, etc. The system 110 may configure the user interface 111 using interactive features, such as the ability for care providers to ask questions or request additional guidance based on the provided feedback.

At step 410, the system 110 may generate predictive analytics based on the integrated patient data, the treatment fidelity scores and/or ratings, and/or the treatment response patterns. In this step, the system 110 may predict potential outcomes of various modifications to a patient's treatment plan, enabling the system to suggest the most effective changes.

To generate predictive analytics, the system 110 may employ various types of machine learning models. In one example approach, the system 110 may use decision trees or random forests, which may be well-suited for modeling complex interactions between variables and predicting outcomes based on multiple input features. The system 110 may train these models using the integrated patient data, treatment fidelity scores, and/or identified response patterns together with outcome data to learn the relationships between these factors and treatment outcomes.

In another example approach, the system 110 may use deep learning models, such as feedforward neural networks or long short-term memory (LSTM) networks, which are able to capture complex, non-linear relationships in data. The system 110 may train these models 115 to predict treatment outcomes based on a wide range of input features, including patient characteristics, treatment history, fidelity scores, and/or response patterns, among the other data described above. Therefore, the system 110 can use these models 115 to uncover subtle patterns and/or interactions that may not be apparent through traditional statistical methods. Moreover, the system 110 may use these models 115 to predict outcomes for patients based on fidelity scores, environmental factors, medical data, and/or the like in various scenarios.

Additionally or alternatively, the system 110 may also use generative models, such as variational autoencoders (VAEs) or generative adversarial networks (GANs), to generate a set of potential modifications to a treatment plan. Because these models can be trained to discover the underlying structure and relationship between the various data (e.g., integrated patient data, treatment fidelity scores, treatment response patterns, etc.), the system 110 can leverage these models to generate new, plausible variations that may improve outcomes. The system 110 may then evaluate the generated treatment plan modifications using predictive models (e.g., as described above) to estimate their potential impact. The system 110 may then rank the various modifications based on impact, as described in more detail for step 412.

Any of the models 115 described above with respect to step 410 may be configured to generate modifications to any aspect of a treatment plan. For example, the models 115 may suggest changing the cadence of data collection, the amount and/or types of data collected, the frequency/schedule of treatment, the care provider, the type of treatment, and/or the like. For example, based on the amount of data for patients and care providers within the integrated data set 202, the system 110 may be able to determine a best match between a patient and care provider based on all of the various factors that are known for the patient and the care provider and then adjust a treatment schedule to include future treatments with the matching care provider. For example, the system 110 may compare treatment fidelity scores for the provider (which may include average scores for certain types of procedures, average scores when working with certain types of patients, etc.) to one or more patient factors (e.g., an upcoming scheduled treatment, a skill acquisition that is part of an individual educational plan, a similarity of the patient to a cluster of other patients, etc.) to determine whether the care provider would be a good match for the patient or not. In embodiments, a specialized model 115 may be trained to predict one or more of these factors. For example, a specialized model 115 may be trained to predict a best match fit between a patient and a care provider based on the large amount of data within the integrated patient data set 202, which may reveal how well other patients and care providers matched (e.g., as revealed by outcomes for similar patients, whether those outcomes improved when changing care providers, and/or other such patterns within the dataset 202).

In some cases, a model 115 may determine that additional information may help improve predictions. Accordingly, the system 110 may modify a treatment plan by requesting and/or requiring the collection of additional data. In some cases, the system 110 may implement this type of change automatically (e.g., by modifying the intake process of FIG. 3).

The treatment fidelity data may play an important role in the predictive analytics process. For example, by incorporating fidelity scores and ratings into the training data and input features, the predictive models 115 and/or generative models 115 may learn how adherence to treatment protocols other measures of treatment fidelity influence patient outcomes. For example, using treatment fidelity data, the models 115 can better differentiate between interventions that did not work because of poor treatment or environmental factors (e.g., meaning the same interventions may have worked in a different context) versus interventions that may not have been appropriate for a particular patient in any condition. Moreover, the system 110 can use the treatment fidelity data to identify specific aspects of the treatment delivery that may need improvement. For instance, if the models detect a strong correlation between low environmental scores (e.g., due to distractions or sensory issues) and poorer outcomes, the predictive analytics might discover and suggest modifications to the treatment setting or environment to enhance effectiveness.

At step 412, the system 110 may generate and/or rank suggested modifications to the treatment plan based on the predictive analytics. In some cases, the system 110 may evaluate the predicted outcomes of various modifications and select the change or changes that are most likely to lead to improved patient outcomes. Additionally or alternatively, the system 110 may consider other factors such as speed and/or efficiency. For example, if one change is predicted to improve an outcome by a certain amount, but requires a large number of treatments over a long period of time, whereas another change is predicted to improve the outcome by a similar amount, but required less time and/or treatments, the system 110 may select the more efficient and/or fast option.

The suggested modifications may encompass a wide range of aspects, such as adjusting the frequency or duration of treatment sessions, incorporating new therapeutic techniques or activities, modifying reinforcement strategies, changing the treatment environment, etc. The system 110 may therefore generate multiple potential modifications and rank them based on their predicted impact, presenting the best options to the care provider first.

In some cases, the system 110 may consider factors such as the feasibility of implementing modifications, a care provider's skills and preferences, and any constraints or limitations specific to the patient or treatment context. In these embodiments, the system 110 may use decision optimization algorithms, such as integer programming or genetic algorithms, to find the best combination of modifications that balances these various factors.

In embodiments, the system 110 may use a language model to generate plain language versions of the suggestions and/or modifications. In embodiments, the language model may be fine-tuned on a corpus comprising any of the data described above and human-generated summaries of the suggestions and/or modifications.

At step 414, the system 110 may output a care provider user interface for display via application 121 presenting the results of the predictive analytics and/or suggested treatment plan modifications. This interface may include visualizations of the predicted outcomes, explanations of the data inputs/reasoning involved in the suggestions (which may be available, for example, if language models are used to summarize suggestions), actionable recommendations for the care provider, and/or the any of the data described above (e.g., in raw form, as visualizations generated by analysis tools, as textual summaries generated by language models, etc.). The user interface may include features such as interactive dashboards, features that allow a user to compare different modification scenarios, and/or the like. The interface may also provide links to additional resources, such as training materials or best practice guidelines, to support the care provider in implementing suggested changes.

In embodiments, a care provider may interactively select which treatment modification plans to approve and/or implement. For example, the care provider may interact with the user interface and approve/disapprove sets of treatment modifications.

Although a care provider may be involved in selecting some modifications to treatment plans, in some cases step 414 may be omitted. For example, the system 110 may, in some situations, automatically adopt treatment plan modifications without waiting for care provider approval or other human approval. For example, depending on the type of adjustment or required timing parameters of the adjustment (e.g., for real-time adjustments), it may be inappropriate or unnecessary to wait for human approval. Accordingly, the operations performed at steps 410-416 as described herein may be automated and performed substantially in real-time. At step 416, the system 110 may take actions to facilitate the implementation of the modified treatment plan (e.g., after confirmation by a care provider, if necessary). For example, the system 110 may automatically schedule care provider training sessions focused on improving any identified weaknesses or areas for improvement. Additionally or alternatively, the system 110 may adjust the scheduling of future patient assessments and/or treatments based on the predicted outcomes and/or the type of approved treatment plan modification. For example, if the predictive analytics suggest that the modifications are likely to lead to rapid improvement, the system may increase the frequency of assessments to closely monitor progress. Conversely, if the modifications are expected to have a more gradual impact, the system 110 may reduce the assessment frequency to avoid unnecessary disruptions to the treatment process.

In some cases, the system 110 may request additional data that may be useful in improving predictions. For example, the system 110 may transmit an immediate request for additional data to a care provider device for display to a care provider.

In embodiments, the system 110 may automatically update various databases and records to reflect the modified treatment plan. For example, the system 110 may update a patient's electronic health record, generate new treatment protocols or session plans, adjust any scheduling or resource allocation systems to ensure that the necessary materials and personnel are available for the modified treatment sessions, and/or the like.

In some cases, a modification to a treatment plan may include instructing data collection devices (e.g., any of devices 120, 130, 140, 150 and/or real-time sensors 520 as discussed in more detail below) to change a cadence (e.g., frequency) of data collection and/or amount of data collection (e.g., granularity and/or other detail level of data collection). In some cases, the system 110 may change the frequency and/or amount of data collection based on real-time analysis to meet the specific needs of the patient or situation. For example, the system 110 may analyze data indicating observed behaviors or physiological parameters to determine fluctuations in these data over time. If the fluctuations (e.g., as indicated by a measure of variability such as a standard deviation, coefficient of variation, rate of change, number and/or severity of detected anomaly, etc.) exceed predefined thresholds, the system 110 may send instructions to one or more of the data-collection devices to increase the sampling rate and thereby receive data more frequently. The increase in data may allow the system to capture more granular data during critical periods when more detailed information is needed to make informed treatment decisions.

For example, in the context of autism therapy, the system may adjust the monitoring frequency of a child's engagement during treatment sessions. If the child exhibits signs of increased stress or agitation (e.g., as indicated by physiological data such as heart rate captured by a heart rate sensor, observed behaviors captured by the assessor, etc.), the system 110 may increase an engagement monitoring frequency from every 5 minutes to every minute. This higher sampling rate enables the system to better capture the child's behavioral responses during high-stress activities, thereby allowing for better detection of patterns and other optimizations.

In another context, namely heart monitoring for a patient with fluctuating heart conditions, the system 110 may dynamically adjust a heart rate monitoring frequency based on a patient's current state. For example, if the system 110 detects indicators of arrhythmia, the system 110 may increase a monitoring frequency from hourly to every 10 minutes. As above, the increased sampling rate may allow for more precise tracking of a patient's heart rate during critical moments, thereby improving interventions and/or treatment adjustments.

In some cases, a modification to a treatment plan may include instructing sensor devices or other devices to change control parameters to adjust an environment of the patient or some other condition. For example, in a behavioral health setting, the system 110 can adjust ambient lighting, temperature, and/or sound levels in real-time during therapeutic sessions based on detected patterns and/or other indicators that environmental conditions may be optimized. For example, based on detecting an increase in a patient's stress indicators (e.g., heart rate or galvanic skin response) and/or detecting associations between patient responses and environmental conditions, the system 110 can determine environmental optimization(s) that adapt the environment to suit the patient's current state. In a specific example, if the system 110 detects a pattern of increased stress indicators that is correlated with increased light levels, the system may automatically dim the lights (e.g., by instructing a light control system) based on the detected pattern. In a similar example, the system 110 may automatically lower the temperature and/or reduce background noise (e.g., by reducing music, shutting automated windows/doors, etc.) based on corresponding environmental factors such as temperature and/or noise levels correlating with increased stress levels. Although these are fairly simple examples, the system 110 may use complex pattern recognition methods as discussed above to discover and then respond to detailed and individualized patterns that may be highly specific to the individual preferences and needs of patients (e.g., personalized patient factors), which some patients (particularly in an ASD context) may have a difficult time communicating, and which may otherwise be highly disruptive to treatment. To adjust the environmental conditions, the system 110 may send instructions to sensor devices that have a control ability (e.g., a thermostat) and/or to separate devices/machines (e.g., an automated lighting system, a security system that controls window/doors, a music player, some other automation system, etc.).

Similarly, if the system 110 is monitoring treatment in a hospital intensive care unit (ICU) setting, the system 110 may modify the settings of various equipment, from automated beds (e.g., which may allow automated control of incline or position), televisions (e.g., to control volume), medical equipment (e.g., to control the settings of respiratory equipment), etc. based on similar detection of individualized patterns. By detecting these individualized patterns (e.g., correlations between environmental factors and personalized patient factors such as stress levels, outcome data indicating treatment effectiveness, etc.), the system 110 can automatically adjust equipment settings to optimize patient treatment, improve care provision, etc.

In some cases, a modification to a treatment plan may include advising program modifiers to implement changes based on insights generated by the system 110. For example, the recommendations generated by predictive analytic models may include various modifications to ongoing programs as discussed above. In some cases, dedicated program modifiers (which may be humans, automated agents, scheduling systems, etc.) may continuously assess whether to implement modifications to a treatment plan for an individual patient. For example, in the context of outdoor therapy for an autistic child, the system 110 may detect, based on behavioral data from previous therapy sessions, a positive correlation between outdoor activities and improved engagement or reduced stress levels. Based on this detected pattern, the system 110 can generate a recommendation to conduct a particular therapy session outdoors in order to optimize the child's response and therapeutic outcomes based on the detected pattern. A program modifier may modify the upcoming session and/or a number of upcoming sessions based on the detected pattern.

In some cases, a modification to a treatment plan may include generating proposed modifications for program designers to modify treatment plans based on cumulative data analysis. In this context, a program designer may modify a treatment plan not only for an individual patient, but for all patients.

For example, the system 110 may aggregate long-term data across multiple sessions to identify effective interventions and areas needing improvement across multiple patients (e.g., all patients, specific sub-populations of patients, etc.). In embodiments, the system 110 may generate and analyze data trends with regard to groups of patient using various clustering methods and thereby identify modifications to an overall treatment protocol that may be effective for many patients. For example, if data consistently indicates better outcomes with specific interventions (e.g., for all patients and/or sub-sets of patients), the system 110 may flag these interventions for inclusion in an updated treatment plans.

As a specific example, in the context of a treatment program for a student with autism, the system 110 may analyze long-term data on a number of students' engagements and performance across various learning activities. If the data consistently shows better engagement and outcomes across student populations or sub-populations in tactile, hands-on learning activities, the system 110 can generate a recommendation to modify the treatment program to incorporate more hands-on learning experiences. Program designers may then review and accept this recommendation to update the treatment plan.

In some cases, the system 110 may implement a modified treatment plan by sending instructions to other systems (e.g., systems 150). For example, if the system 110 determines that an optimized treatment schedule should be implemented, the system 110 may send the optimized treatment schedule to a system 150 that handles scheduling for the patient. The optimizing treatment plan may indicate, for example, a different time and/or frequency of treatments, a different set of care providers (e.g., the optimized treatment schedule may be optimized to match the availability of a best match care provider for the patient), and/or any other scheduling factor.

Example Real-Time Monitoring System

Figure 5:
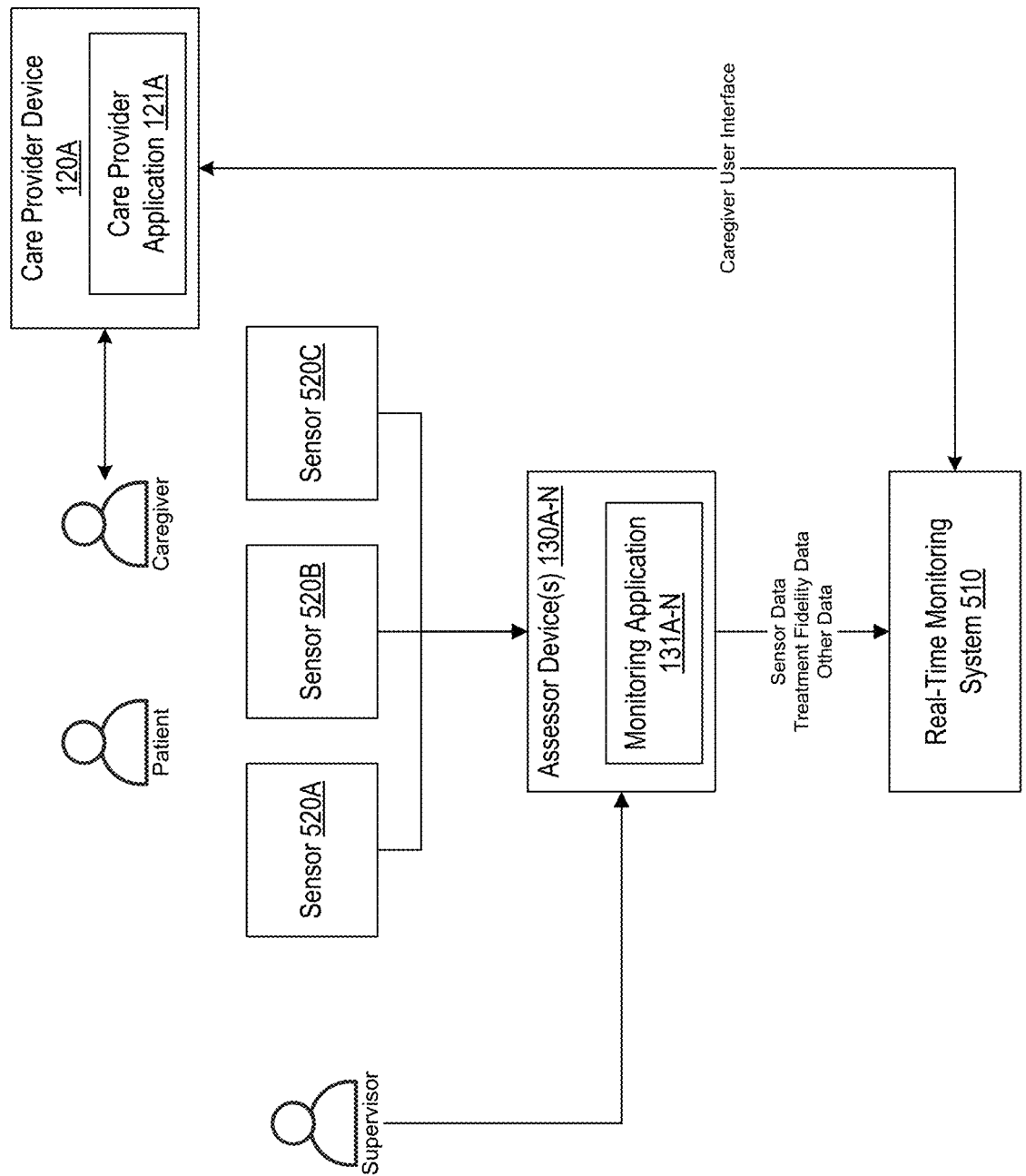
FIG. 5 illustrates an example environment including a real-time monitoring system as described within the present disclosure.

FIG. 5 illustrates an example embodiments that includes a real-time monitoring system 510 that performs inference as described earlier to provide real-time feedback to a care provider during treatment, enabling treatment optimization that leverages treatment fidelity data and the methods described above. The real-time monitoring system 510 can be an implementation of the system 110, incorporating the various features and functionalities described throughout the disclosure for the system 110. Additionally, the real-time monitoring system 510 can be further configured with real-time functionality and any additional functions necessary for the operations described below.

As shown in FIG. 5, the real-time monitoring system 510 receives data, including sensor data, treatment fidelity data, and other data, from one or more assessor devices 130A-N. In embodiments, this data may be received in real time (e.g., as a continuous stream of data and/or regular updates).

In some cases, an assessor device 130 may be a device used by an assessor who is overseeing the treatment. The assessor can use the device to input real-time assessments of treatment fidelity indicating whether the treatment is proceeding according to a plan, whether procedures are being performed correctly, whether the care provider is maintaining professionalism, whether any environmental issues exist or not, etc. The assessor can fill out survey items or respond to questions throughout the treatment, manually monitoring the session and providing treatment fidelity data, for example by using the various treatment fidelity assessments described above.

Additionally or alternatively, the assessor devices 130 may receive data from one or more sensors, such as sensors 520A, 520B, and 520C, as shown in the figure. These sensors can capture various types of data in real-time during the treatment or assessment. For example, a sensor could be a microphone collecting audio data, a camera capturing video data, a device measuring environmental factors such as noise levels or temperature, etc. The sensors can gather any relevant data in the vicinity of the treatment involving the patient and the care provider. In some cases, additional data may be received from other devices, such as a patient device 140 (e.g., a smart watch) or any other device capable of providing real-time data for analysis.

In embodiments, one or more assessor devices 130 may receive the sensor data, and each of the one or mor devices 130 may be equipped with a monitoring application 131. For example, a single device 130 may handle multiple data streams from multiple sensors 520 and/or any input data from the assessor. Alternatively, separate devices 130 may handle different types of sensor data and/or a separate device 140 may handle the assessor's input. In some cases, the assessor devices 130 may perform processing of the sensor data before forwarding it to the real-time monitoring system 510 for further analysis.

In embodiments, the devices 130 and/or the monitoring system 510 may perform real-time analyses on the sensor data to generate real-time treatment fidelity data updates and/or other data updates. For example, the devices 130 and/or 510 may monitor video or audio data to assess the care provider's adherence to treatment procedures, (e.g., in a simple example, the video may be analyzed to verify that the care provider is maintaining eye contact during treatment, the audio may be analyzed to verify that the care provider uses a neutral tone of voice, etc.), responding appropriately to the patient's activities, following specific protocols, and/or the like. In some cases, the system may be pre-configured by the assessor or care provider (e.g., using the monitoring application 131 on the assessor device 130 or the care provider application 121 on the care provider device 120) to look for specific behaviors, procedures, or interactions during the treatment session based on a treatment plan. For example, the pre-configuration may indicate that certain procedures are scheduled for a treatment, that certain patient behaviors should be recognized and responded to using a specific procedure or set of procedures, and/or the like.

To analyze the sensor data in real-time, the systems 130 and/or 510 may use multimodal models capable of processing video, audio, and/or text data. For example, if the video or audio data captures the patient engaging in a targeted behavior, the system may use a multimodal model 115 to recognize that behavior in real-time. In some cases, inputs to the multimodal model may include one or more images taken from the video, one or more audio snippets, text generated based on speed within the audio (e.g., using speech-to-text algorithms), etc. In embodiments, the device 130 and/or 510 may repeatedly (e.g., N number of times per second) prompt the multimodal model with a set of items or behaviors to recognize and request the model to generate an output indicating which of the set of items or behaviors are recognized.

As another example, the device 130 and/or 510 can use multimodal models 115 to evaluate the care provider's response to certain patient behaviors or adherence to specific treatment procedures. For example, after recognizing a targeted behavior, the device 130 and/or 510 may repeatedly (e.g., N number of times per second) prompt the multimodal model to analyze whether the caretaker has responded to the targeted behavior or not and/or is using a designated procedure to respond to the behavior. The multimodal model may respond by outputting one or more indications of whether a procedure is being followed.

The real-time monitoring system 510 may perform real-time inference using any of the various steps described in FIG. 4 based on the data streaming in from the assessor devices 130 and/or any other relevant data sources. In embodiments, this real-time data may be combined with existing patient data in an integrated patient data set 202 to provide inputs to various models 115. The system 510 can execute any or all of the inference steps described above for FIG. 4 in a continuous loop or at some frequency (e.g. X times per second or minute) to generate real-time insights and feedback for the care provider.

As the treatment fidelity data, sensor data, and other relevant data are fed into the real-time monitoring system 510, the system 510 updates the various inputs that are provided into the various models discussed in FIG. 4 to generate updated analyses including real-time outputs. The system may provide these outputs to the care provider device 120A for display via the care provider application 121A, giving the care provider immediate feedback and guidance during the treatment session.

As a simple example, if the system 510 detects that the care provider has missed a step in a procedure or failed to follow a protocol correctly, the system 510 can send a notification to the care provider device 120A prompting the care provider to go back and redo the procedure or to respond in a specific way the next time the patient exhibits a targeted behavior. Accordingly, the system 510 can provide corrective feedback that can help the care provider stay on track and ensure that all necessary steps are completed. Moreover, because the system 510 allows for continuous collection and analysis of data, the system 510 may continue receiving additional real-time sensor data and may analyze the additional data to verify that the procedure was redone correctly. As a specific example, if a procedure calls for a care provider to ask a certain question to a patient when the patient engages in a targeted behavior, the system 510 may initially detect the patient engaging in the targeted behavior (e.g., based on a visual observation of the patient from video by a multimodal model, based on text analysis of an automatically-generated audio transcript fed into a language model, and/or based on the assessor logging the targeted behavior in the assessor device 130). The system 510 may then analyze the next few seconds (e.g., 30 seconds) of sensor data to determine if the care provider asked the prescribed question (e.g., based on text analysis of an automatically-generated audio transcript fed into a language model). If the system 510 determines that the care provider did not ask the prescribed question, it may prompt the care provider to ask the prescribed question immediately and/or at the next time the patient engages in the targeted behavior (where the choice may depend on the procedure) via the care provider device 120. Then, the system 510 may continue receiving additional sensor data and may use the additional sensor data to verify that the procedure was followed correctly (e.g., because the care provider asks the missed question immediately and/or the next time the patient engages in the targeted behavior).

Additionally, the system 510 may use the real-time inference to detect more subtle patterns and trends that may not be immediately apparent to the care provider. For example, the system 510 can continuously monitor treatment fidelity scores (which may be updated in real-time as new data is received), such as a clinical score, environmental score, and/or professionalism score. If the system 510 detects that one of these scores is declining over time and/or falls below a certain threshold, the system 510 can trigger an alert on the care provider device 120A, notifying the care provider of the issue and potentially providing insights into the factors contributing to the decline. This real-time detection and alerts may allow the care provider to consider the reasons for the reduction in score and work to improve treatment fidelity.

Additionally, if the system 510 identifies any treatment response patterns in real-time, such as correlations between specific care provider behaviors and patient outcomes, the system 510 may display an indicator of the identified treatment response pattern on the care provider device 120A. The care provider may then use this information to, for example, reinforce positive patterns and/or mitigate negative ones.

The real-time monitoring system 510 can also continuously update the predictive analytics and/or treatment plan modification suggestions based on the incoming data updates. As the treatment progresses and new data is collected, the system can provide better predictions and recommendations. In some cases, the system 510 can generate a dynamically updated list of suggested actions and interventions, where the suggestions may be ranked based on their predicted effectiveness and displayed on the care provider device 120A.

Accordingly, by leveraging the large amount of data that may be collected through sensors and other sources, and combining it with the comprehensive data described elsewhere in the disclosure, the real-time monitoring system 510 enables a highly responsive and adaptive treatment approach. The system's ability to analyze treatment fidelity, detect response patterns, generate predictive analytics, and suggest treatment modifications in real-time enables care providers to make rapid adjustments and improvements to the treatment based on the specific needs and progress of each individual patient. The real-time feedback loop may react to changes in the patient's behavior, environmental factors, treatment effectiveness, and other factors.

Specific Example Scenarios

Although a wide variety of improvements are enabled using the above systems and methods, this section includes a few simplified examples to illustrate some of the functionalities enabled by the techniques described herein.

In a first example scenario illustrating the use of treatment fidelity data, a patient (Ava, 6 years old) may be working with a technician (John) and assessor (Dr. Lee, observing the session). The system 110 may log an error because John provided an incorrect level of prompt during a task. This error may be manually observed and recorded by Dr. Lee and/or detected by various sensors. Based on this detected error, the system 110 may generate care provider feedback that suggests specific training modules for John to improve his prompting techniques. Additionally, the system 110 may identify a patient-specific pattern where Ava responds positively to a specific type of prompt that John often omits. The system 110 may predict an improved outcome if the missed prompt is consistently applied, and suggest that John increase the frequency of specific prompts.

In a second example scenario illustrating the use of treatment fidelity data together with external data, a patient (Ethan, 4 years old, diagnosed with Autism) may be working with a technician (Jane). Ethan's medical or other data (e.g., IoT data) may indicate recent sleep issues. The system 110 may detect a pattern of discrepancies between Jane's application of standard procedures during Ethan's crisis behaviors, which correlate with the recent sleep issues. The system 110 may accordingly suggest modifications to Jane's treatment approach during Ethan's low-responsiveness periods, focusing on gentler and more engaging techniques that align better with Ethan's current state.

In a third example scenario illustrating a modification to a treatment plan, a patient (Mia, 7 years old) may be working with a technician (David) on a program for social skills development. The system 110 may detect a treatment pattern where Mia engages more during one-on-one sessions than group sessions (e.g., based on audio analysis and/or data logged by David or David's supervisor). Based on the pattern and recorded progress for Mia, the system 110 may recommend a revised treatment plan that includes more one-on-one peer interactions.

CONCLUSION

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

The methods and systems described herein may be deployed in part or in whole through a system that executes computer software, program codes, and/or instructions on a processor. The present disclosure may be implemented as a method on the system, as a subsystem or apparatus as part of or in relation to the system, or as a computer program product embodied in a computer readable medium executing on one or more of the systems. In embodiments, the processor may be part of a server, cloud server, client, network infrastructure, mobile computing platform, stationary computing platform, or other computing platforms. A processor may be any kind of computational or processing device capable of executing program instructions, codes, binary instructions and the like, including a central processing unit (CPU), a general processing unit (GPU), a logic board, a chip (e.g., a graphics chip, a video processing chip, a data compression chip, or the like), a chipset, a controller, a system-on-chip (e.g., an RF system on chip, an AI system on chip, a video processing system on chip, or others), an integrated circuit, an application specific integrated circuit (ASIC), a field programmable gate array (FPGA), an approximate computing processor, a quantum computing processor, a parallel computing processor, a neural network processor, or other type of processor. The processor may be or may include a signal processor, digital processor, data processor, embedded processor, microprocessor or any variant such as a co-processor (math co-processor, graphic co-processor, communication co-processor, video co-processor, AI co-processor, and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor, or any system utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache, network-attached storage, server-based storage, and the like.

A processor may include one or more cores that may enhance speed and performance of a multiprocessor. In embodiments, the process may be a dual core processor, quad core processors, other chip-level multiprocessor and the like that combine two or more independent cores (sometimes called a die).

The methods and systems described herein may be deployed in part or in whole through a system that executes computer software on a server, client, firewall, gateway, hub, router, switch, infrastructure-as-a-service, platform-as-a-service, or other such computer and/or networking hardware or system. The software may be associated with a server that may include a file server, print server, domain server, internet server, intranet server, cloud server, infrastructure-as-a-service server, platform-as-a-service server, web server, and other variants such as secondary server, host server, distributed server, failover server, backup server, server farm, and the like. The server may include one or more of memories, processors, computer readable media, storage media, ports (physical and virtual), communication devices, and interfaces capable of accessing other servers, clients, systems, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, systems, and devices through a wired or a wireless medium, and the like. The methods, programs, or codes as described herein and elsewhere may be executed by the client. In addition, other devices required for the execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network with multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, 4G, 5G, LTE, EVDO, mesh, or other network types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic book readers, music players and the like. These devices may include, apart from other components, a storage medium such as flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, network-attached storage, network storage, NVME-accessible storage, PCIE connected storage, distributed storage, and the like.

The methods and systems described herein may transform physical and/or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on systems through computer executable code using a processor capable of executing program instructions stored thereon as a monolithic software structure, as standalone software modules, or as modules that employ external routines, code, services, and so forth, or any combination of these, and all such implementations may be within the scope of the present disclosure. Examples of such systems may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices, artificial intelligence, computing devices, networking equipment, servers, routers and the like. Furthermore, the elements depicted in the flow chart and block diagrams or any other logical component may be implemented on a system capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other system capable of executing program instructions. Computer software may employ virtualization, virtual machines, containers, dock facilities, portainers, and other capabilities.

Thus, in one aspect, methods described above and combinations thereof may be embodied in computer executable code that, when executing on one or more computing devices, performs the steps thereof. In another aspect, the methods may be embodied in systems that perform the steps thereof and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "with," "including," and "containing" are to be construed as open-ended terms (i.e., meaning "including, but not limited to,") unless otherwise noted. Recitations of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. The term "set" may include a set with a single member. No language in the specification should be construed as indicating any non-claimed element as essential to the practice of the disclosure.

While the foregoing written description enables one skilled to make and use what is considered presently to be the best mode thereof, those skilled in the art will understand and appreciate the existence of variations, combinations, and equivalents of the specific embodiment, method, and examples herein. The disclosure should therefore not be limited by the above-described embodiment, method, and examples, but by all embodiments and methods within the scope and spirit of the disclosure.

All documents referenced herein are hereby incorporated by reference as if fully set forth herein.

The invention claimed is:

1. A computer-implemented method comprising:
   receiving patient data for a patient being treated for autism spectrum disorder (ASD);
   receiving, from one or more sensors, sensor data during a behavioral treatment session involving a care provider for the patient being treated for ASD;
   generating treatment fidelity data based on the sensor data from the one or more sensors, wherein the treatment fidelity data is generated using a first machine learning model, wherein the generated treatment fidelity data includes a plurality of indicators of whether the care provider is following a treatment plan for the behavioral treatment session;
   generating, based on the patient data and the treatment fidelity data, using a second machine learning model, a plurality of treatment fidelity scores including:
      an environmental score that is indicative of environmental conditions that may interfere with the behavioral treatment session;
   determining, based on the environmental score, that the treatment plan is not optimized;
   generating, using a predictive analytics model, based on the patient data, an optimized treatment plan to mitigate an environmental factor that inhibits treatment effectiveness, wherein the optimized treatment plan includes one or more adjustments to environmental conditions during treatment;
   transmitting, to a machine that controls environmental conditions in a vicinity of the patient, an instruction to adjust at least one of the environmental conditions to mitigate the environmental factor that inhibits treatment effectiveness; and
   controlling the machine to physically adjust the at least one of the environmental conditions to mitigate the environmental factor that inhibits treatment effectiveness.

2. The method of claim 1, wherein the optimized treatment plan includes a future treatment session with a different care provider, wherein generating the optimized treatment plan comprises matching the patient with the different care provider based on the patient data and a respective treatment fidelity score associated with the different care provider.

3. The method of claim 1, wherein the one or more sensors include a video sensor, wherein the first machine learning model is a multimodal model that accepts image data.

4. The method of claim 1, wherein the one or more sensors include an audio sensor, wherein the first machine learning model is a language model.

5. The method of claim 1, wherein determining that the treatment plan is not optimized comprises detecting a reduction in the environmental score.

6. The method of claim 1, further comprising:
   detecting, based on environmental data within the patient data, an individualized pattern indicating a correlation between at least one of the environmental conditions and a personalized patient factor, wherein the generating the optimized treatment plan is based on the individualized pattern.

7. The method of claim 1, wherein the patient data further includes medical data for the patient, environmental data indicating environmental conditions of the patient, behavioral health data for the patient, and outcome data indicating one or more outcomes for the patient.

8. A computer-implemented method comprising:
   receiving patient data for a patient being treated for a condition, wherein the patient data comprises environmental data collected by sensors during treatment;
   receiving treatment fidelity data including a plurality of indicators of whether a care provider is following a treatment plan for a behavioral treatment session;
   generating, based on the patient data and the treatment fidelity data, using a machine learning model, a plurality of treatment fidelity scores including an environmental score that is indicative of environmental conditions that may interfere with the behavioral treatment session;
   determining, based on the environmental score, that the environmental conditions are not optimized for treatment;
   detecting, based on the environmental data, an individualized pattern indicating a correlation between at least one of the environmental conditions and a personalized patient factor;
   generating, based on the individualized pattern, an instruction to adjust the at least one of the environmental conditions by controlling a machine in a vicinity of the behavioral treatment session to mitigate an environmental factor that inhibits treatment effectiveness;
   transmitting the instruction to the machine to mitigate the environmental factor that inhibits treatment effectiveness; and
   upon receiving the instruction, controlling the machine to physically adjust the at least one of the environmental conditions in the vicinity of the behavioral treatment session to mitigate the environmental factor that inhibits its treatment effectiveness.

9. The method of claim 8, wherein the machine is a thermostat that controls heating or cooling.

10. The method of claim 8, wherein the machine is an automation system that controls lighting.

11. The method of claim 8, further comprising:
generating, using a predictive analytics model, based on the patient data, an optimized treatment plan, wherein the optimized treatment plan includes a modified treatment schedule; and
transmitting, to a treatment scheduling system, an instruction to adopt the modified treatment schedule.

12. The method of claim 8, wherein the patient data further includes medical data for the patient behavioral health data for the patient, and outcome data indicating one or more outcomes for the patient.

13. The method of claim 8, wherein the personalized patient factor is an indicator of an increase in stress levels for the patient.

14. The method of claim 8, wherein the personalized patient factor is an indicator of a decrease in treatment effectiveness for the patient.

15. A computer-implemented method comprising:
receiving patient data for a patient being treated for a condition;
receiving, from one or more sensors, real-time sensor data during a behavioral treatment session involving a care provider for the patient being treated for the condition;
generating treatment fidelity data based on the real-time sensor data from the one or more sensors, wherein the treatment fidelity data is generated using a machine learning model, wherein the generated treatment fidelity data includes an environmental score for the behavioral treatment session;
detecting, based on the treatment fidelity data, that one or more environmental conditions are inhibiting treatment effectiveness;
adjusting, using at least one environmental control machine in a vicinity of the patient, the one or more environmental conditions that are inhibiting treatment effectiveness;
receiving additional real-time sensor data after adjusting the one or more environmental conditions; and
verifying, based on the additional real-time sensor data, a mitigation of the one or more environmental conditions that are inhibiting treatment effectiveness.

16. The method of claim 15, further comprising:
generating, based on the patient data and the treatment fidelity data, using a second machine learning model, a plurality of treatment fidelity scores including:
a clinical score that is indicative of whether the care provider is accurately following clinical procedures;
the environmental score, wherein the environmental score is indicative of the one or more environmental conditions that are inhibiting treatment effectiveness; and
a professionalism score that is indicative of professionalism of the care provider.

17. The method of claim 16, further comprising detecting that the care provider did not correctly follow a treatment plan for the behavior treatment session by detecting a drop in the clinical score.

18. The method of claim 15, wherein the one or more sensors include a video sensor, wherein the machine learning model is a multimodal model that accepts image data.

19. The method of claim 15, wherein the one or more sensors include an audio sensor, wherein the machine learning model is a language model.

* * * * *